(12) United States Patent
Keller et al.

(10) Patent No.: US 7,723,454 B2
(45) Date of Patent: May 25, 2010

(54) COATING OF ORGANIC FIBERS WITH SILOXANE-CARBORANE POLYMERS

(75) Inventors: Teddy M Keller, Fairfax Station, VA (US); Manoj K. Kolel-Veetil, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 833 days.

(21) Appl. No.: 11/468,331

(22) Filed: Aug. 30, 2006

(65) Prior Publication Data

US 2009/0239070 A1    Sep. 24, 2009

Related U.S. Application Data

(63) Continuation-in-part of application No. 10/874,000, filed on Jun. 22, 2004, now Pat. No. 7,238,766, application No. 11/468,331, filed on Aug. 30, 2006, which is a continuation-in-part of application No. 10/923,153, filed on Aug. 18, 2004, now Pat. No. 7,153,921, application No. 11/468,331.

(60) Provisional application No. 60/541,017, filed on Feb. 3, 2004, provisional application No. 60/597,355, filed on Nov. 28, 2005.

(51) Int. Cl.
 *C08G 77/56* (2006.01)
(52) U.S. Cl. .................... 528/5; 528/32; 528/31
(58) Field of Classification Search ............ 528/5, 528/32, 31
See application file for complete search history.

(56) References Cited

U.S. PATENT DOCUMENTS

| | | | |
|---|---|---|---|
| 5,272,237 A | 12/1993 | Keller et al. | |
| 5,292,779 A | 3/1994 | Keller et al. | |
| 5,483,017 A | 1/1996 | Keller et al. | |
| 5,552,505 A | 9/1996 | Keller | |
| 5,563,181 A | 10/1996 | Keller et al. | |
| 5,679,818 A | 10/1997 | Bucca et al. | |
| 5,681,870 A | 10/1997 | Keller et al. | |
| 5,756,629 A | 5/1998 | Keller et al. | |
| 5,780,569 A | 7/1998 | Keller et al. | |
| 5,807,953 A | 9/1998 | Bucca et al. | |
| 5,844,052 A | 12/1998 | Keller et al. | |
| 5,874,514 A | 2/1999 | Keller et al. | |
| 5,932,335 A | 8/1999 | Keller et al. | |
| 5,969,072 A | 10/1999 | Keller et al. | |
| 5,981,678 A | 11/1999 | Keller et al. | |
| 5,986,032 A | 11/1999 | Keller et al. | |
| 6,025,453 A | 2/2000 | Keller et al. | |
| 6,187,703 B1 | 2/2001 | Keller et al. | |
| 6,187,890 B1 | 2/2001 | Fehn et al. | |
| 6,225,247 B1 | 5/2001 | Keller et al. | |
| 6,362,289 B1 | 3/2002 | Keller et al. | |
| 6,495,483 B1 | 12/2002 | Keller et al. | |
| 6,770,583 B2 | 8/2004 | Keller | |
| 6,787,615 B2 | 9/2004 | Keller et al. | |
| 6,967,233 B2 | 11/2005 | Keller | |
| 7,411,030 B2 | 8/2008 | Keller | |
| 2005/0148750 A1* | 7/2005 | Keller | 528/5 |
| 2005/0171316 A1 | 8/2005 | Keller et al. | |
| 2005/0171317 A1 | 8/2005 | Keller et al. | |
| 2009/0082490 A1 | 3/2009 | Keller | |

OTHER PUBLICATIONS

Henderson et al., "Synthesis and Characterization of Poly(carborane-siloxane-acetylene)" Macromolecules, 27(6), 1660-1661 (1994).
Kolel-Veetil et al., "Formation of elastomeric network polymers from ambient heterogeneous hydrosilations of carboranylenesiloxane and branched siloxane monomers" J. Polym. Sci. Part A: Polym. Chem. 44(1),147-155 (2006).
U.S. Appl. No. 11/239,448, filed Sep. 27, 2005.
U.S. Appl. No. 11/468,367, filed Aug. 30, 2006.
Office action in U.S. Appl. No. 11/468,367, filed Jul. 2009.
U.S. Appl. No. 12/633,854, filed Dec. 2009.

* cited by examiner

*Primary Examiner*—Kuo-Liang Peng
(74) *Attorney, Agent, or Firm*—Amy L. Ressing; Joseph T. Grunkemeyer

(57) ABSTRACT

A fiber of linear polymer coated with a siloxane-carborane polymer or a thermoset or ceramic made therefrom. An organic fiber coated with a siloxane-carborane polymer or a thermoset or ceramic made therefrom and a surfactant. An organic fiber coated with a siloxane-carborane polymer made from a hydrosilation reaction of a siloxane-carborane compound containing at least two unsaturated carbon-carbon bonds and a silane compound or a thermoset or ceramic made therefrom. A method of coating a fiber by contacting a fiber to an aqueous solution of a siloxane-carborane polymer and a surfactant or to a solution of a siloxane-carborane polymer in a non-halogenated organic solvent. A method of contacting a fiber to a solution of a siloxane-carborane polymer, drying the coating to a temperature that does not change the polymer to a thermoset or ceramic, and using the dried, coated fiber in a process that requires that the fiber be flexible.

24 Claims, 5 Drawing Sheets

COATING OF ORGANIC FIBERS WITH SILOXANE-CARBORANE POLYMERS

This application claims the benefit of U.S. Provisional Patent Application No. 60/597,355, filed on Nov. 28, 2005, incorporated herein by reference. This application is a continuation-in-part application of U.S. patent application Ser. No. 10/874,000, filed on Jun. 22, 2004, pending, which claims the benefit of U.S. Provisional Patent Application No. 60/541,017, filed on Feb. 3, 2004, all incorporated herein by reference. This application is a continuation-in-part application of U.S. patent application Ser. No. 10/923,153, filed on Aug. 18, 2004, pending, which claims the benefit of U.S. Provisional Patent Application No. 60/541,017, filed on Feb. 3, 2004, all incorporated herein by reference.

FIELD OF THE INVENTION

The invention is generally related to siloxane-carborane polymer-coated fibers.

DESCRIPTION OF RELATED ART

The need for high performance organic fibers in demanding applications is an ever growing one. In the defense industry organic fibers for high performance applications include, but are not limited to, ZYLON® (Eq. (1)), KEVLAR® (Eq. (2)), carbon/graphite fibers, and SPECTRA® ultra high molecular weight polyethylene. Although ZYLON®, KEVLAR®, and SPECTRA® have found increasing use in ballistic vests and armor, carbon fibers is by far the most widely used.

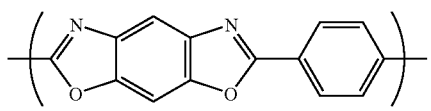

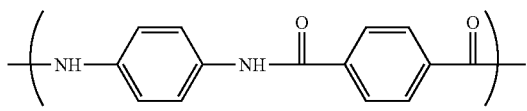

The chemical structures of the available man-made organic fibers reflect a broad diversity in the nature of the repeating linkages between reactive organic functional groups contained in the fibers. ZYLON® is a linear rigid rod polymer of poly(benzobisoxazole), specifically poly(p-phenylene-2,6-benzobisoxazole). KEVLAR® is an amide linked polymer with the linkages between repeating dicarboxylic and diamine aromatic units, specifically poly(p-phenylene terephthalamide). The fiber is further strengthened by intermolecular hydrogen bonding. M5® is a rigid rod polymer that combines some of the properties of ZYLON® and KEVLAR®. The fiber, poly(pyridobisimidazole-2,6-diyl-(2,5-dihydroxy-p-phenylene)) (Eq. (3)), is very similar in structure to ZYLON®. In addition, the fiber contains hydrogen bonds in two mutually perpendicular directions rendering it stronger than ZYLON®.

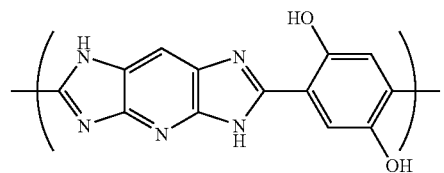

Carbon fiber consists of extended sheath of fused ring structures produced by the initial oxidation around 300° C. in air of poly(acrylonitrile) (PAN) leading to a ladder polymer and its subsequent carbonization (graphitization) in an inert atmosphere up to 3000° C. to produce fibers containing nearly 100% carbon. VECTRA® (poly(4-oxybenzoate-co-2,6-oxynaphthoate), Eq. (4)) is made wholly of aromatic polyester and the fiber DACRON® is a polyester derived from the condensation of ethylene glycol and terephthalic acid (Eq. (5)).

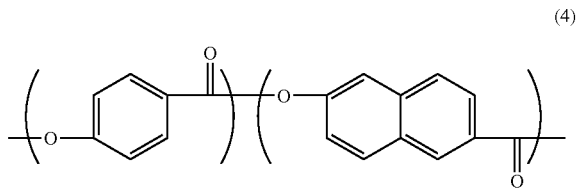

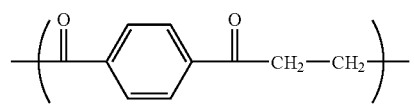

Some of the applications of the aramid fiber KEVLAR® include its use apparel, fire resistant mattress material, performance apparel, adhesives and sealants, ballistics and defense, belts and hoses, composites, fiber-optic and electro-mechanical cables, friction products and gaskets, protective apparel, tires, ropes, and cables. Similarly, ZYLON® is used in protective clothing (protective clothing for firefighters, safety gloves, heat-resistant clothing, body armor, protective gloves for electric works), sports goods (sail cloth, yacht ropes, tennis rackets and strings, ski poles, fishing rods, jeans, racing suits, racing cars, golf clubs), aerospace (balloon, aircraft engine fragment barrier, satellite), industrial materials (heat resistant felt, optical fiber cable, sling, cable jacket for welding machine, reinforcement for belts and tires and reinforcement for cements), speaker cones, sewing thread, and protection for high voltage rubber gloves. SPECTRA® or DYNEMA® is used as the super-fine, super-strong, ultra-lightweight fibers for armor, aerospace and high performance sporting good applications. VECTRA® is used in ropes and cables, industrial/military/aerospace applications and in sporting goods. Carbon fibers are mainly used in high performance composites.

Of these fibers, ZYLON® possesses the best mechanical characteristics, including the highest Young's modulus (270 GPa; and compression strength=300 MPa) along the chain axis (Krause et al., "Morphology and properties of rigid-rod poly(p-phenylene benzobisoxazole) (PBO) and stiff-chain poly(2,5(6)-benzoxazole) (ABPBO) fibres" *Polymer*, 29(8), 1354-1364 (1988). All referenced publications and patent documents are incorporated herein by reference.) (Table 1).

M5® (Young's modulus=330-350 GPa and compression strength=3500-4500 MPa) has better mechanical and thermal properties than ZYLON®.

TABLE 1

| Fiber | Tensile modulus (GPa) |
|---|---|
| carbon | 234-537 |
| M5 ® | >350 |
| ZYLON ® | 180-270 |
| KEVLAR ® | 83-186 |
| SPECTRA ® | 172 |
| VECTRA ® | 110 |

While all of these fibers perform well under an ambient atmosphere up to a reasonably high temperature, they catastrophically decompose in air in the temperature range of 450-625° C. (Bourbigot et al., "Heat resistance and flammability of high performance fibres: A review" *Fire Mater.*, 26(4), 155-168 (2002)). The catastrophic degradation/failure of KEVLAR®, ZYLON®, and carbon fibers is shown in FIG. 1. Hence, a utilization of these fibers in air for applications at or above this temperature range may only become a reality if these fibers are protected against oxidation.

SUMMARY OF THE INVENTION

The invention comprises a coated fiber comprising: a fiber comprising a linear polymer and a coating on the fiber comprising a siloxane-carborane polymer or a thermoset or ceramic made therefrom.

The invention further comprises a coated fiber comprising: an organic fiber and a coating on the fiber comprising a siloxane-carborane polymer or a thermoset or ceramic made therefrom and a surfactant.

The invention further comprises a coated fiber comprising: an organic fiber and a coating on the fiber comprising a siloxane-carborane polymer or a thermoset or ceramic made therefrom. The siloxane-carborane polymer or thermoset or ceramic made therefrom is made from a hydrosilation reaction of a siloxane-carborane compound containing at least two unsaturated carbon-carbon bonds and a silane compound.

The invention further comprises a method of coating a fiber comprising contacting a fiber to an aqueous solution of a siloxane-carborane polymer and a surfactant to coat the fiber with the solution.

The invention further comprises a method of coating a fiber comprising contacting a fiber to a solution of a siloxane-carborane polymer in a non-halogenated organic solvent to coat the fiber with the solution.

The invention further comprises a method comprising: contacting a fiber to a solution of a siloxane-carborane polymer to coat the fiber with the solution, drying the coating to a temperature that does not change the polymer to a thermoset or ceramic, and using the dried, coated fiber in a process that requires that the fiber be flexible.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
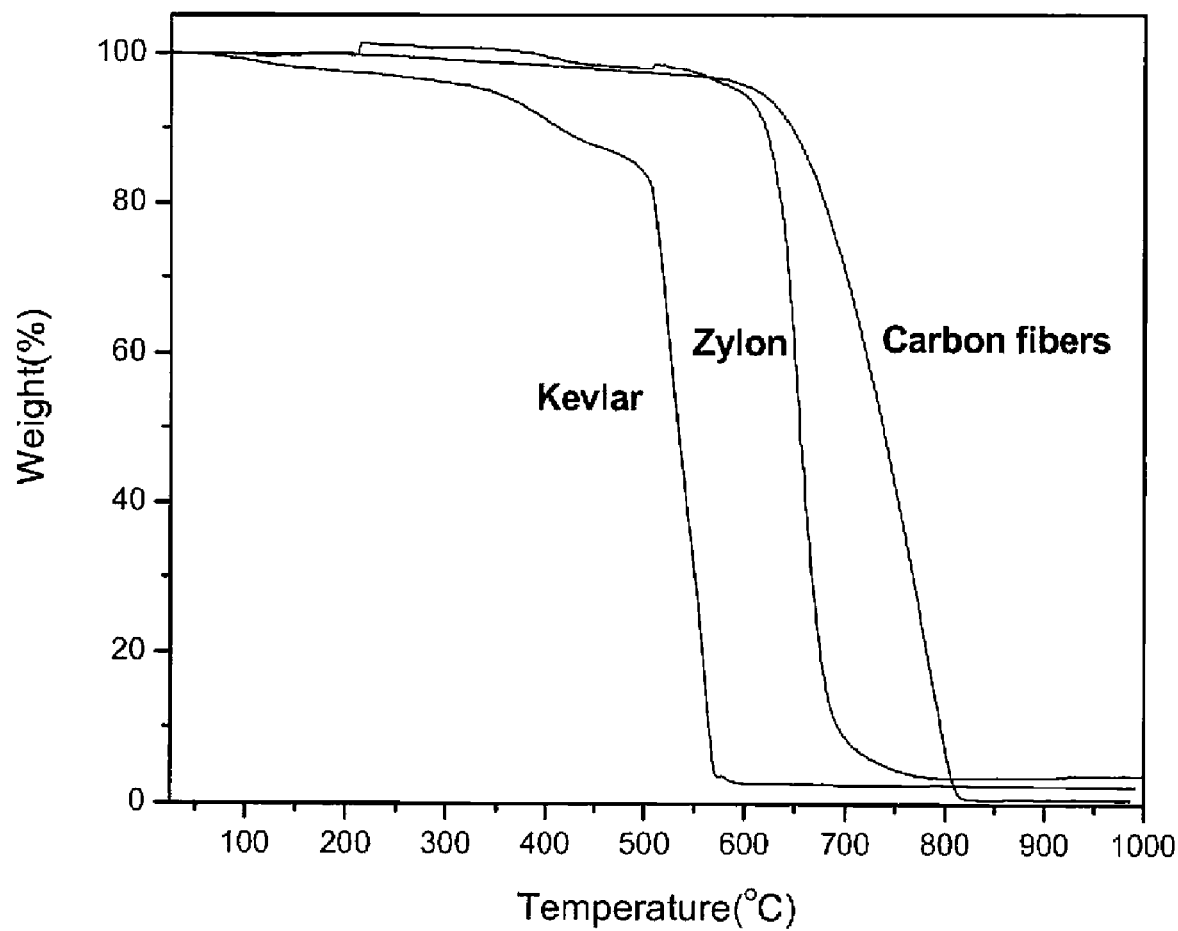
FIG. 1 shows thermograms depicting the oxidative degradation (in the range 450-750° C.) of KEVLAR®, ZYLON®, and carbon fibers.
Figure 2:
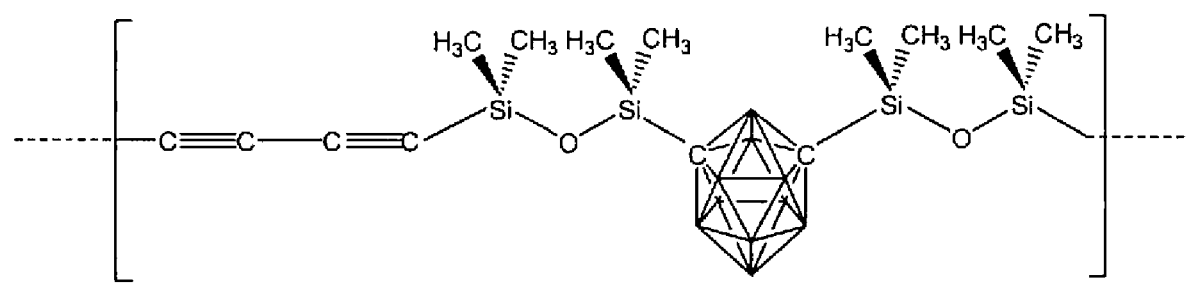
FIG. 2 shows the structure and thermogram of a diacetylene-containing carboranylenesiloxane.
Figure 2:
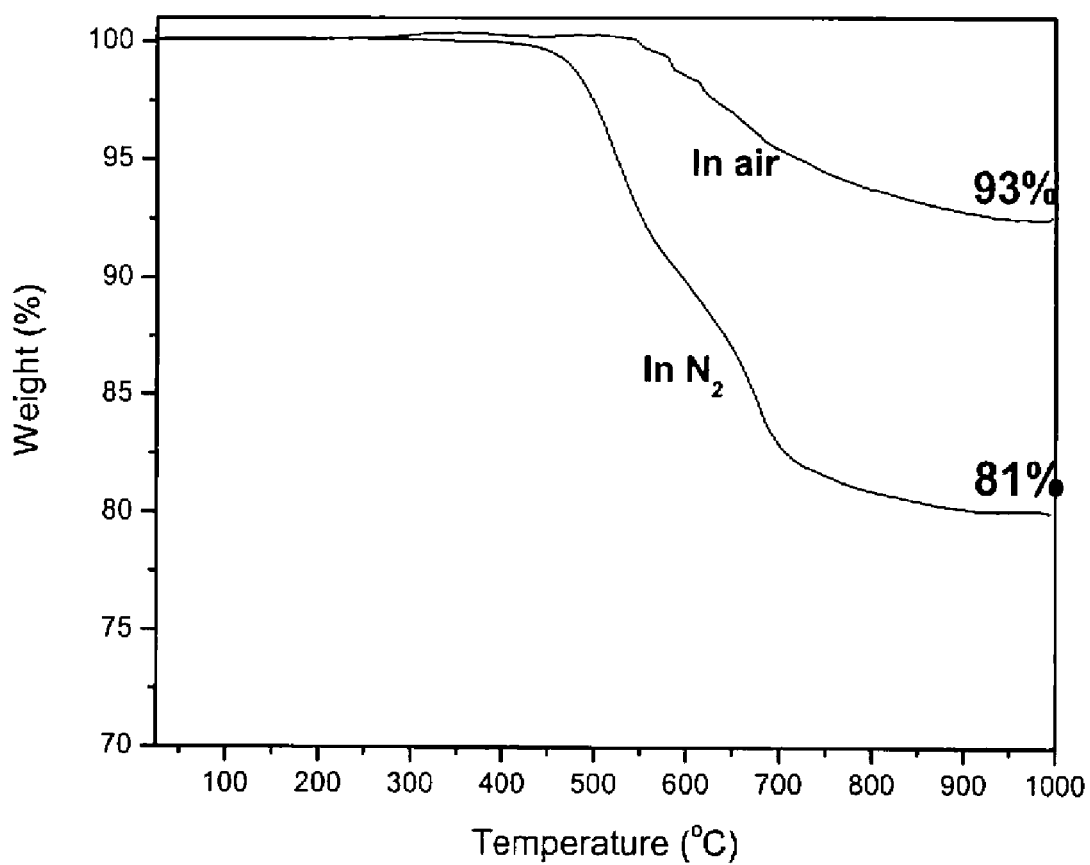
Figure 3:
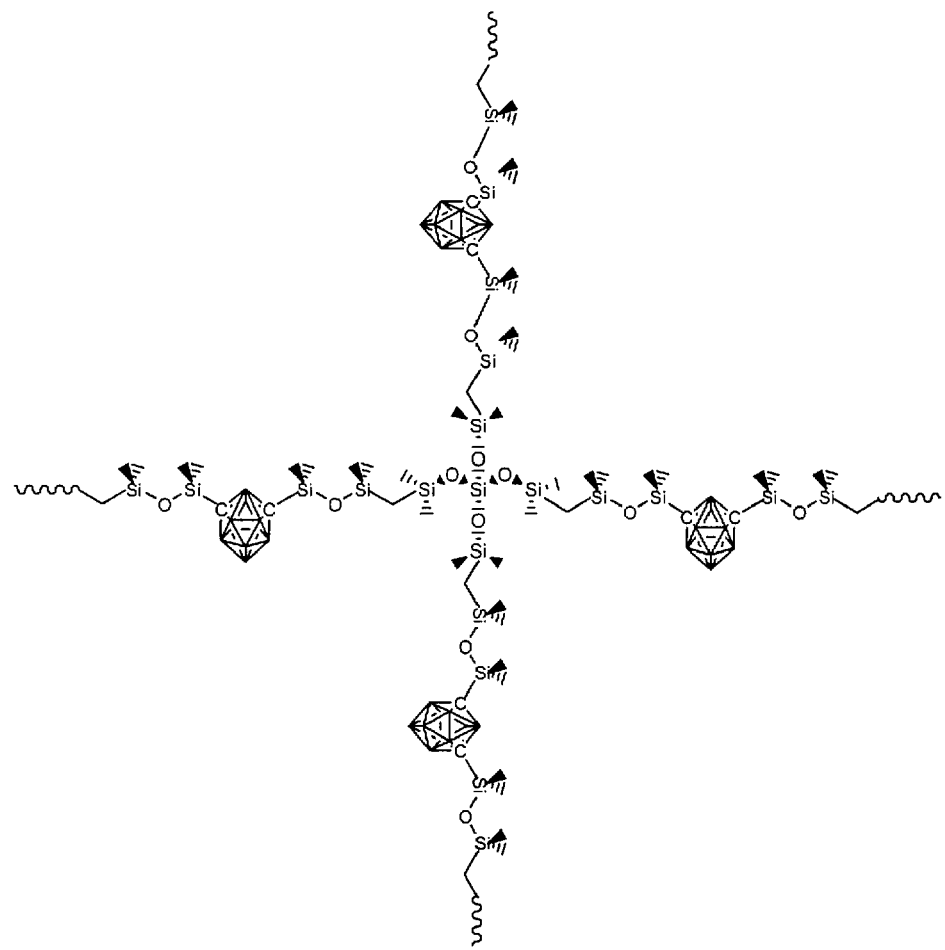
FIG. 3 shows the structure and thermogram of a hydrosilatively-crosslinked carboranylenesiloxane network.
Figure 3:
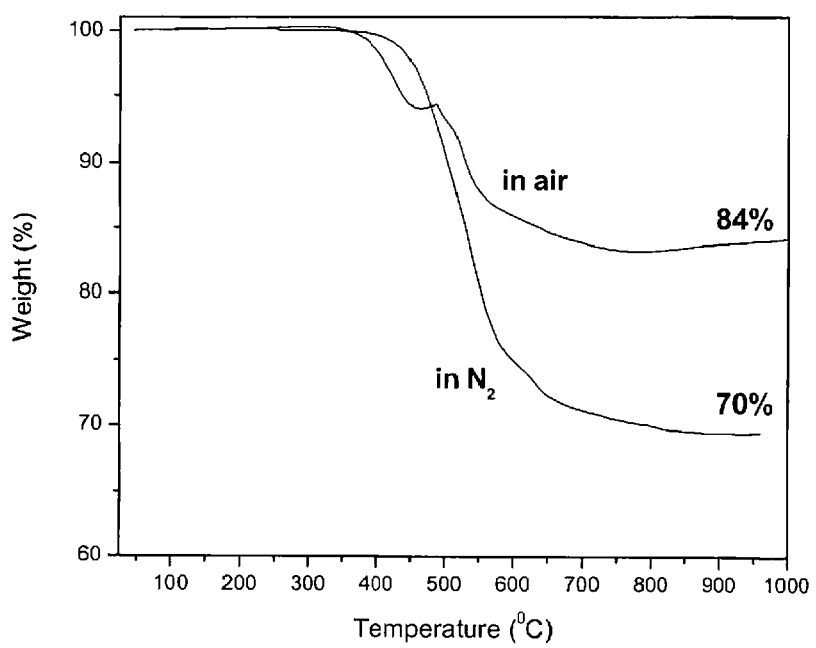

Organic fibers, which include but are not limited to those mentioned above, may be protected against thermo-oxidative degradation by the application of a siloxane-carborane polymer, which may form a thermo-oxidatively stable coating that can resist such a catastrophic degradation. The polymer may protect the fiber from oxygen and/or moisture. ZYLON® in particular is sensitive to moisture. Diacetylene-containing poly(carboranylenesiloxane)s and the hydrosilatively networked poly(carboranylenesiloxane)s are groups of polymers that can have exceptional thermal and thermo-oxidative stabilities (Henderson et al., "Synthesis and Characterization of Poly(carborane-siloxane-acetylene)" *Macromolecules*, 27(6), 1660-1661 (1994); Kolel-Veetil et al., *Polymer Preprints*, 45(1), 579-580 (2004); Kolel-Veetil et al., "Formation of elastomeric network polymers from ambient heterogeneous hydrosilations of carboranylenesiloxane and branched siloxane monomers" *J. Polym. Sci. Part A: Polym. Chem.* 44(1), 147-155 (2006)). The carborane and the crosslinked network-imparted thermo-oxidative stabilities can render these systems exceptionally thermally stable even to temperatures in excess of 1500° C. FIG. 2 shows the structure and thermogram of a diacetylene-containing carboranylenesiloxane. FIG. 3 shows the structure and thermogram of a hydrosilatively-crosslinked carboranylenesiloxane network.

Suitable organic fibers include, but are not limited to, carbon fibers, high performance fibers, and linear polymeric fibers. Carbon fibers are not linear polymeric fibers. Suitable linear polymeric fibers include, but are not limited to, poly(p-phenylene-2,6-benzobisoxazole), poly(p-phenylene terephthalamide), high molecular weight polyethylene, poly(4-oxybenzoate-co-2,6-oxynaphthoate), polyethylene terephthalate, or poly(pyridobisimidazole-2,6-diyl-(2,5-dihydroxy-p-phenylene)). Combinations of fibers or fibers containing multiple different compounds may be used.

The networks in two types of carboranylenesiloxanes are produced by the thermal polymerization of the diacetylene groups (Eq. (6)) or by the hydrosilation of vinyl or ethynyl carboranylenesiloxanes (Eq. (7)). (As used herein, polyhedral chemical structures contain boron atoms at the vertices unless shown as carbon atoms.) The utilization of these two thermo-oxidatively stable network polymers as protective coatings for high performance organic fibers may improve the performance of the fibers in air at elevated temperatures. Mixtures and copolymers of the polymers may also be used. Any polymer that contains at least 2 of a described repeat unit or contains at least 50 mol % of such repeat unit is considered to be a polymer of the repeat unit.

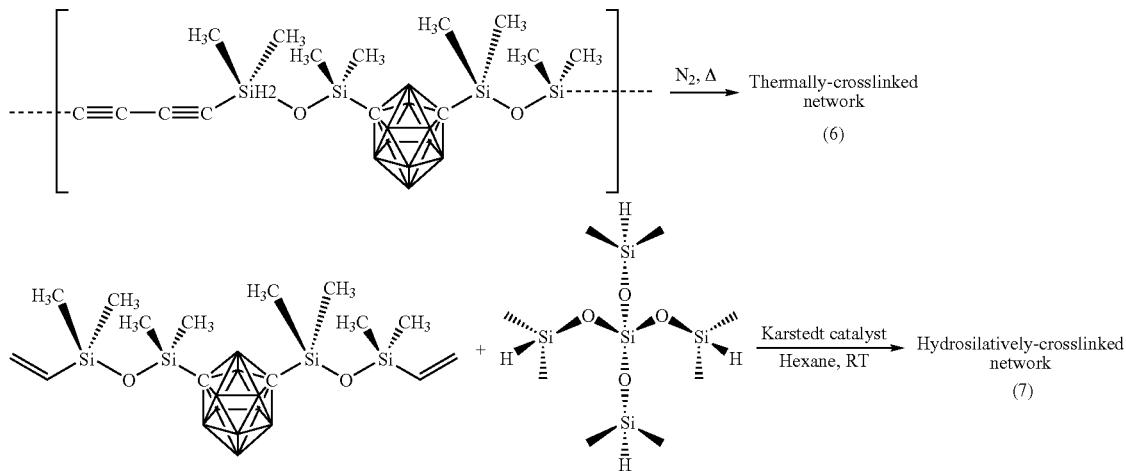

(6)

(7)

A general formula for the polymer in Eq. (6) is —{C≡C—C≡C—(SiR$_2$—O)$_m$—SiR$_2$—[CB$_{10}$H$_{10}$C—SiR$_2$—(O—SiR$_2$)$_m$]$_p$}$_n$—. Each R is an independently selected organic group, and each m, each p, and n are independently selected positive integers. Suitable polymers include those where each R is methyl, each m is 1, 2, or 3, and each p is 1 or 2.

The hydrosilation polymers include, but are not limited to, those where the siloxane-carborane compound has the formula U—(SiR$_2$—O)$_m$—SiR$_2$—CB$_{10}$H$_{10}$C—SiR$_2$—(O—SiR$_2$)$_m$—U; and the silane compound has the formula H—SiR$_2$—(O—SiR$^1$R$^2$)$_n$—O—SiR$_2$—H. Each R is an independently selected organic group. Each R$^1$ is independently selected from H, R, methyl, phenyl, and —O—SiR$_2$—H. Each R$^2$ is independently selected from H, R, methyl, and —O—SiR$_2$—H. Each U is an independently selected group containing an unsaturated carbon-carbon bond. Each m and n is an independently selected positive integer. Suitable polymers include those where each R is methyl, each m is 1, and each U is vinyl or ethynyl. Suitable crosslinkers include, but are not limited to, tetrakis(dimethylsiloxyl)silane, methyltris(dimethylsiloxyl)silane, phenyltris(dimethylsiloxyl)silane, and 1,1,3,3,5,5-hexamethyltrisiloxane.

Any of the siloxane-carborane polymers disclosed in any of U.S. Pat. Nos. 5,272,237; 5,292,779; 5,348,917; 5,483,017; 5,552,505; 5,563,181; 5,679,818; 5,681,870; 5,756,629; 5,780,569; 5,807,953; 5,844,052; 5,874,514; 5,932,335; 5,969,072; 5,981,678; 5,986,032; 6,025,453; 6,187,703; 6,225,247; 6,265,336; 6,362,289; 6,495,483; 6,579,955; 6,767,981; 6,770,583; 6,784,259; 6,784,270; 6,787,615; 6,967,233; US Patent Application Publication Nos. 2005/0171316 and 2005/0171317; and U.S. patent application Ser. No. 11/239,448 may be applicable. Various carboranylenesiloxane monomers and oligomers, and branched siloxane crosslinkers that may be utilized are represented in Eqs. (8)-(16). The vertices of the polyhedral structures are boron atoms unless shovel as carbon.

(8)

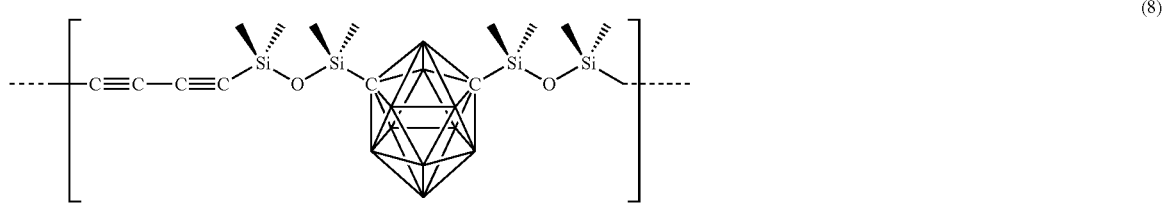

1

(9)

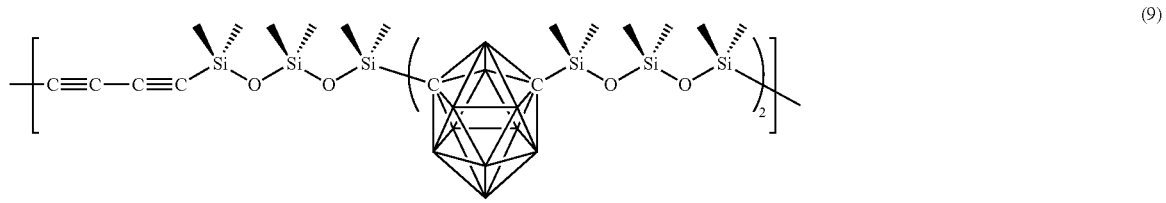

2

-continued

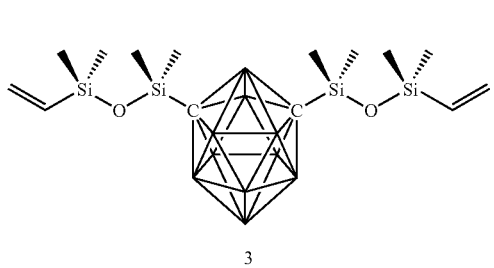

(10)

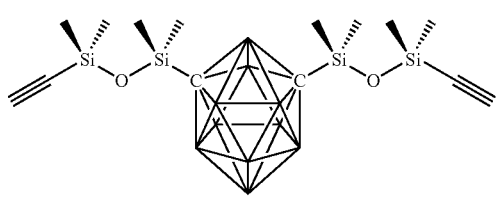

(11)

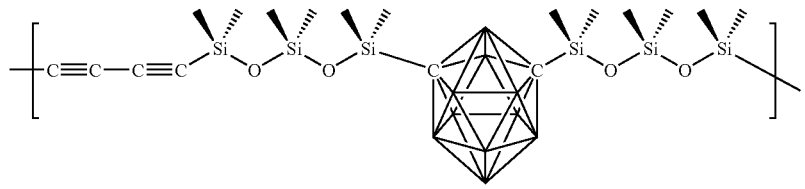

(12)

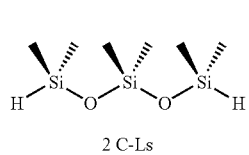

2 C-Ls (13)

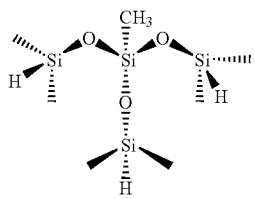

3 C-Ls/Me (14)

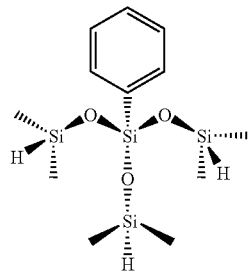

3 C-Ls/Ph (15)

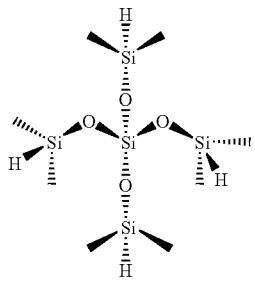

4 C-Ls (16)

The coatings on the organic fibers resulting from the thermal curing of the diacetylene-containing carboranylenesiloxanes typically were darker in appearance, while the coatings resulting from the hydrosilation-derived carboranylenesiloxane networks typically were clear in appearance. Hence, a selection between the two choices can be made based on the desirability of the nature of appearance of the coating in addition to the extent of the afforded thermo-oxidative protection.

Figure 4:
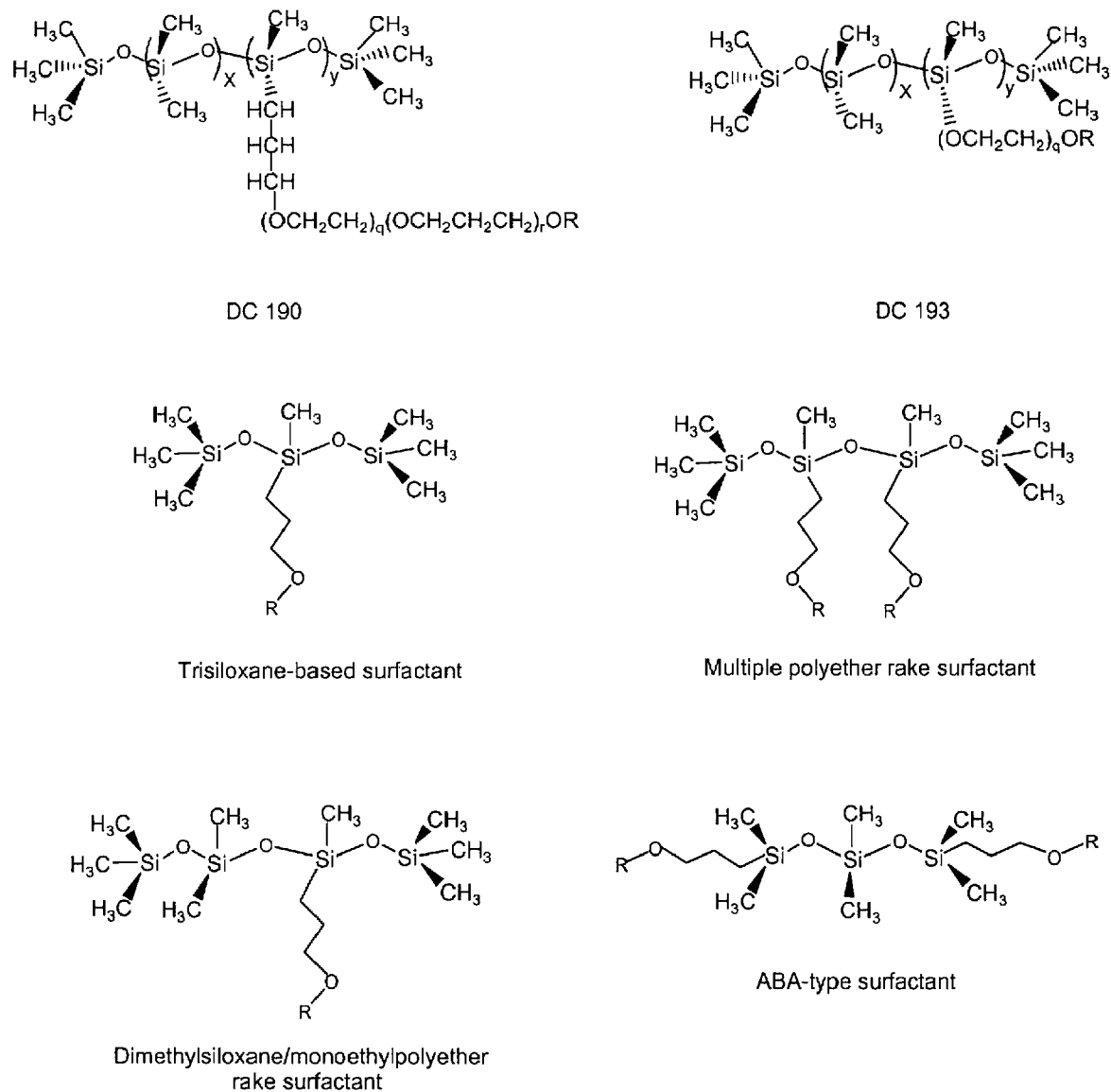
FIGS. 4 and 5 show example surfactants.
Figure 5:
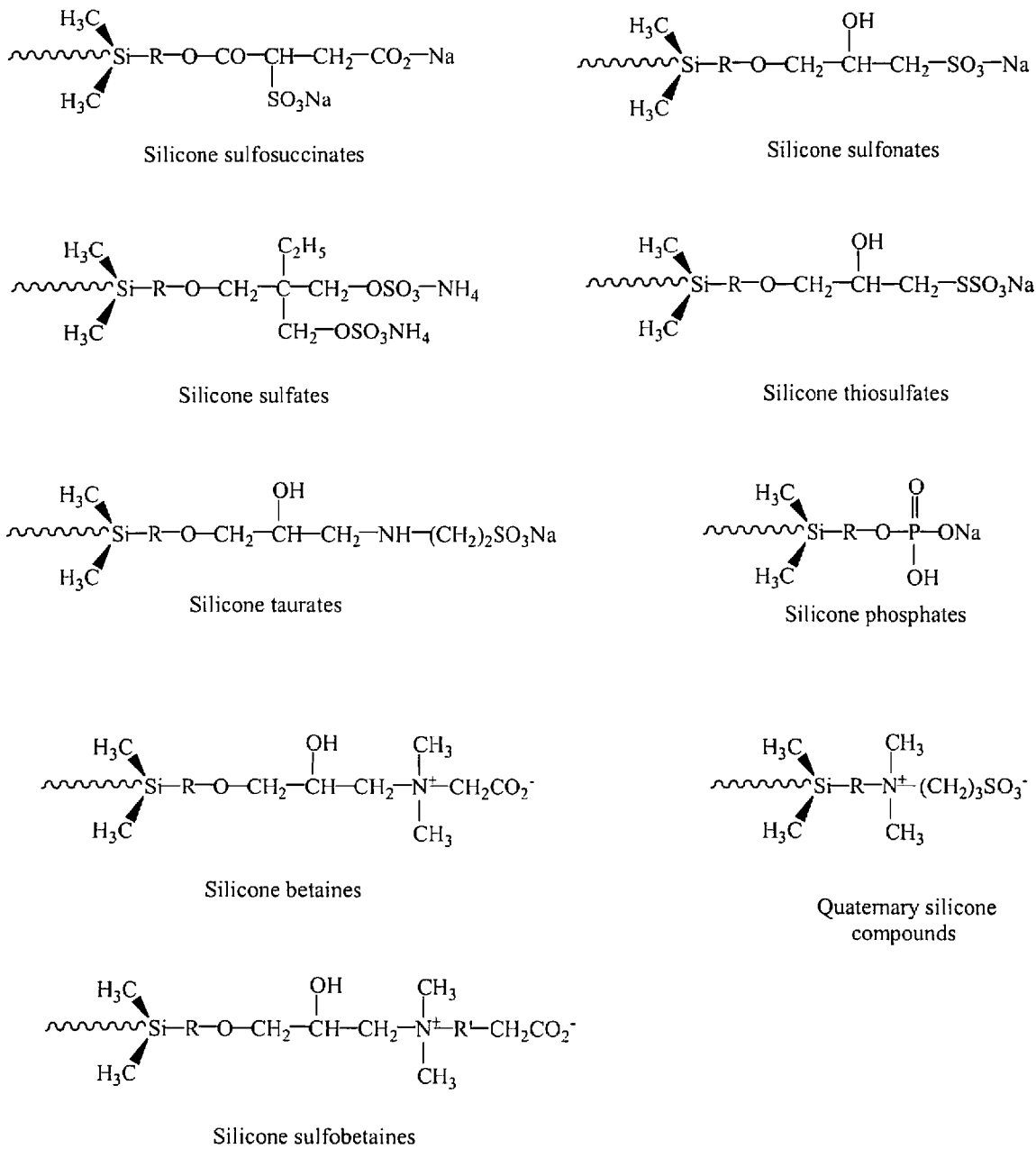

The coating may comprise a surfactant, such as a surfactant that comprises silicon. Suitable surfactants include, but are not limited to, those shown in FIGS. 4 and 5. For DC 190 and DC 193, the values of p, q, x, and y are average numbers of the respective repeat units. When the coating is a ceramic form of the polymer, it may contain the surfactant in form that is also ceramic and incorporated into the ceramic form of the polymer. The surfactant may be useful when coating the fiber with an aqueous solution of the polymer. Other suitable surfactants include, but are not limited to, phosphorous-containing surfactants, boron-containing surfactants, anionic surfactant, cationic surfactants, and charge-neutral surfactants.

The surfactant may be incorporated into the coating by, for example, sonicating the polymer with the surfactant then dissolving this mixture in water. The fiber is then coated with this aqueous mixture. Alternatively, the polymer and surfactant may be dissolved in an organic solvent, such as diethyl ether, followed by evaporation of the solvent to form a residue and dissolution in water.

The fiber may also be coated by a solution of the polymer in an organic solvent, including but not limited to, non-halogenated organic solvents such as hexane, xylene, and diethyl ether. A surfactant typically does not improve the coating when an organic solvent is used.

The wet coating on the fiber may be dried to a temperature that changes the polymer to a thermoset or ceramic. Alternatively, it may be dried to a temperature that does not change the polymer to a thermoset or ceramic. The polymer-coated fiber may then be used in a process that requires the fiber be flexible. For example, the fiber may need to be wound onto spool for storage. A thermoset- or ceramic-coated fiber may be stiff such that storage of long lengths of fiber would be impracticable. If a thermoset- or ceramic-coated fiber is ultimately needed or is the natural result of the use of the fiber, then such conversion may take place after the polymer-coated fiber is unwound from the spool for such use.

Having described the invention, the following examples are given to illustrate specific applications of the invention. These specific examples are not intended to limit the scope of the invention described in this application.

General Procedures—The syntheses of the oligomeric inorganic-organic hybrid polymers PCSA (Disiloxyl/1:2:1) (1, Eq. (8)), PCSA (Trisiloxyl/2:3:1) (2, Eq. (9)), and PCSA (Trisiloxyl/2:1:1) (5, Eq. (11)) were based on published procedures of similar oligomers in Kolel-Veetil, et al., "The Effects of Concentration Dilution of Cross-linkable Diacetylenes on the Plasticity of Poly(m-Carborane-Disiloxane-Diacetylene)s" *J. Mater. Chem.*, 13, 1652-1656 (2003) and Kolel-Veetil, et al., "Dependence of Thermal Properties on Copolymer Sequence in Diacetylene-Containing Polycarboranylene-siloxanes" *Chem. Mater.*, 16, 3162-3167, (2004). The synthesis of 1,7-bis(vinyltetramethyldisiloxyl)m-carborane (3, Eq. (10)) and 1,7-bis(ethynyltetramethyldisiloxyl)m-carborane (4, Eq. (11)) were following the published procedures disclosed in Houser et al., "Hydrosilation routes to materials with high thermal and oxidative stabilities" *J. Polym. Sci.: Part A: Polym. Chem.*, 36(11), 1969-1972 (1998) and Keller et al., U.S. Pat. No. 5,981,678 (1998). Tetrakis (dimethylsiloxyl)silane (4 C-Ls, Eq. (16)), methyltris(dimethylsiloxyl)silane (3 C-Ls/Me, Eq. (14)), phenyltris(dimethylsiloxyl)silane (3 C-Ls/Ph, Eq. (15)) and 1,1,3,3,5,5-hexamethyltrisiloxane (2 C-Ls, Eq. (13)) were used as received from Gelest. The hydrosilation reactions were performed based on published procedures in Kolel-Veetil et al., *J. Polym. Sci.: Part A: Polym. Chem.*, 44(1), 147-155 (2006). The surfactants DC 190 and DC 193 were obtained from Dow Corning and were used as received.

Thermogravimetric analyses (TGA) were performed on a SDT 2960 simultaneous DTA-TGA analyzer. Differential scanning calorimetry (DSC) studies were conducted on a DSC 2920 modulated DSC instrument. All thermal experiments were carried out at a heating rate of 10° C./min and a nitrogen flow rate of 100 cc/min. Infrared (IR) spectra were obtained on thin films deposited on NaCl disks using a Nicolet Magna 750 Fourier transform infrared spectrometer. Solution-state $^1$H NMR and $^{13}$C NMR spectra (of 3 and 4) were acquired on a Bruker AC-300 spectrometer and referenced to the internal solvent peak (CDCl$_3$).

The tension tests at room temperature were done using an in-house load applying machine with the tested fibers being gripped between a Capstan action grip set procured from MTS Systems, MN. The tension tests at simultaneous applied load and temperature were done using an in-house instrument with attached thermocouples.

The fibers ZYLON® (Toyobo, Ltd.), SPECTRA® (Honeywell Corporation), VECTRA® (Goodfellow Corporation), KEVLAR® (DuPont Corporation), optical fiber (Corning Corporation and Fiberoptic System, Inc. Simi Valley, Calif.), and carbon fibers (Fibraplex Corporation) were used as received.

Example 1

TGA evaluation of thermo-oxidative protection of ZYLON® fiber/tows on application of a single coating using a 0.05 M solution of (1) in CH$_2$Cl$_2$—Fiber drying: ZYLON® fiber/tows were severed into small pieces of ~11 mg each and were dried in a TGA instrument at 400° C. for 4 h under an atmosphere of nitrogen. (Note: A darkening of the yellowish tow is observed on drying. The dried fiber had a purplish hue to it. Some deleterious effects on the tow from the reaction at a higher temperature of residual moisture and polyphosphoric acid in it cannot be discounted). A 15% loss was observed in the weight of the ZYLON® fiber/tow after drying.

Preparation of the coating solution: 0.114 g of polymer 1 was dissolved in 5 mL of CH$_2$Cl$_2$ to yield a 0.05 M solution of the material.

Coating of the ZYLON® fiber tows with the PCSA solution and the curing of the deposited coating: The cut pieces of ZYLON® fiber/tows were immersed for 5 minutes in the PCSA solution taken in a 5 mL vial. After this, the fiber was taken out, air dried for an hour and held twice for 20 sec each in a hot air blast from a heat gun. The fiber was weighed to estimate the weight of the deposited coating (e.g.: Weight of the fiber/tow before coating=0.0103 g. Weight of the fiber/tow after coating=0.0110 g. Hence, the respective weight and % by weight of the coating are 0.0007 g and 6.8). The coated fiber was thermally treated in a TGA instrument under an inert atmosphere initially at 250° C. for 30 min and subsequently at 400° C. for 120 min having taken to the respective temperature at 110° C./min. (Note: When more than a single coating is desired, the coating and curing procedures can be repeated prior to the test for thermo-oxidative stability of the fiber/tow).

Thermo-oxidative stability test of the 1-coated ZYLON® fiber/tow—Treatment to 1000° C. in air in a TGA instrument: The PCSA-coated ZYLON® fiber/tow was heated under air in a TGA instrument to 1000° C. at 10° C./min. Weight retention=10%. This represents a 3.2% weight retention of the ZYLON® fiber/tow at 1000° C. (In comparison, under similar conditions, an uncoated ZYLON® fiber/tow is completely oxidized by 750° C.).

Example 2

TGA evaluation of thermo-oxidative protection of ZYLON® fiber/tows on application of three coatings using a 0.2 M solution of 1 in CH$_2$Cl$_2$—The weight of the ZYLON® fiber/tow tested was 0.0117 g. 0.456 g of polymer 1 was dissolved in 5 mL of CH$_2$Cl$_2$ to yield a 0.2 M solution of the material. The procedure for coating with the PCSA solution and the subsequent curing of the ZYLON® fiber/tow was as in Example 1 which was repeated three times and the weight of the coating was found to be 0.003 g (25% by weight of the fiber/tow). The thermo-oxidative stability test of the coated fiber/tow was performed as in Example 1. A weight retention of 72% was obtained.

Example 3

TGA evaluation of thermo-oxidative protection of ZYLON® fiber/tows on application of four coatings using a 0.2 M solution of 1 in CH$_2$Cl$_2$—The weight of the ZYLON® fiber/tow tested was 0.0113 g. Four coatings of the PCSA polymer was obtained as described in Example 1. The weight of the coating was found to be 0.0033 g (29% by weight of the fiber/tow). The thermo-oxidative stability test of the coated fiber/tow was performed as in Example 1. A weight retention of 78% was obtained.

Example 4

TGA evaluation of thermo-oxidative protection of ZYLON® fiber/tows on application of a single coating using a 0.5 M solution of 2 in CH$_2$Cl$_2$—The weight of the ZYLON® fiber/tow tested was 0.0296 g. 1.5 g of the polymer 2 was dissolved in 5 mL of CH$_2$Cl$_2$ to yield a 0.5 M solution of the material. The procedure for coating with the PCSA solution and the subsequent curing of the ZYLON® fiber/tow was as in Example 1 and the weight of the coating was found to be 0.007 g (24% by weight of the fiber/tow). The thermo-oxidative stability test of the coated fiber/tow was performed as in Example 1. A weight retention of 60% was obtained.

Example 5

TGA evaluation of thermo-oxidative protection of ZYLON® fiber/tows on application of two coatings using a 0.5 M solution of 2 in $CH_2Cl_2$—The weight of the ZYLON® fiber/tow tested was 0.0260 g. Two coatings of the PCSA polymer was obtained as described in Example 1. The weight of the coating was found to be 0.0075 g (29% by weight of the fiber/tow). The thermo-oxidative stability test of the coated fiber/tow was performed as in Example 1. A weight retention of 66% was obtained.

Example 6

TGA evaluation of thermo-oxidative protection of ZYLON® fiber/tows on application of three coatings using a 0.5 M solution of 2 in $CH_2Cl_2$—The weight of the ZYLON® fiber/tow tested was 0.0232 g. Two coatings of the PCSA polymer was obtained as described in Example 1. The weight of the coating was found to be 0.0075 g (32% by weight of the fiber/tow). The thermo-oxidative stability test of the coated fiber/tow was performed as in Example 1. A weight retention of 68% was obtained.

Example 7

TGA evaluation of thermo-oxidative protection of ZYLON® fiber/tows on application of three coatings using a 0.5 M solution of 2 in hexane—The weight of the ZYLON® fiber/tow tested was 0.0241 g. Two coatings of the PCSA polymer was obtained as described in Example 1. The weight of the coating was found to be 0.007 g (29% by weight of the fiber/tow). The thermo-oxidative stability test of the coated fiber/tow was performed as in Example 1. A weight retention of 67% was obtained.

Example 8

TGA evaluation of thermo-oxidative protection of ZYLON® fiber/tows on application of three coatings using a 0.5 M solution of 2 in xylene—The weight of the ZYLON® fiber/tow tested was 0.0239 g. Two coatings of the PCSA polymer was obtained as described in Example 1. The weight of the coating was found to be 0.0075 g (31% by weight of the fiber/tow). The thermo-oxidative stability test of the coated fiber/tow was performed as in Example 1. A weight retention of 69% was obtained.

Example 9

TGA evaluation of thermo-oxidative protection of ZYLON® fiber/tows on application of three coatings using a 0.5 M solution of 2 in diethyl ether—The weight of the ZYLON® fiber/tow tested was 0.0232 g. Two coatings of the PCSA polymer was obtained as described in Example 1. The weight of the coating was found to be 0.007 g (30% by weight of the fiber/tow). The thermo-oxidative stability test of the coated fiber/tow was performed as in Example 1. A weight retention of 68% was obtained.

Example 10

TGA evaluation of thermo-oxidative protection of KEVLAR® fiber/tows on application of a single coating using a 0.2 M solution of 1 in $CH_2Cl_2$—The weight of the KEVLAR® fiber/tow tested was 0.0151 g. The procedure for coating with the PCSA solution and the subsequent curing of the ZYLON® fiber/tow was as in Example 1 and the weight of the coating was found to be 0.004 g (26% by weight of the fiber/tow). The thermo-oxidative stability test of the coated fiber/tow was performed as in Example 1. A weight retention of 42% was obtained.

Example 11

TGA evaluation of thermo-oxidative protection of KEVLAR® fiber/tows on application of two coatings using a 0.2 M solution of 1 in $CH_2Cl_2$—The weight of the KEVLAR® fiber/tow tested was 0.0163 g. Two coatings of the PCSA polymer was obtained as described in Example 1. The weight of the coating was found to be 0.0045 g (28% by weight of the fiber/tow). The thermo-oxidative stability test of the coated fiber/tow was performed as in Example 1. A weight retention of 51% was obtained.

Example 12

TGA evaluation of thermo-oxidative protection of KEVLAR® fiber/tows on application of three coatings using a 0.2 M solution of 1 in $CH_2Cl_2$—The weight of the KEVLAR® fiber/tow tested was 0.0159 g. Two coatings of the PCSA polymer was obtained as described in Example 1. The weight of the coating was found to be 0.005 g (31% by weight of the fiber/tow). The thermo-oxidative stability test of the coated fiber/tow was performed as in Example 1. A weight retention of 62% was obtained.

Example 13

TGA evaluation of thermo-oxidative protection of SPECTRA® fiber/tows on application of a single coating using a 0.2 M solution of 1 in $CH_2Cl_2$—The weight of the SPECTRA® fiber/tow tested was 0.0163 g. The procedure for coating with the PCSA solution and the subsequent curing of the ZYLON® fiber/tow was as in Example 1 and the weight of the coating was found to be 0.004 g (25% by weight of the fiber/tow). The thermo-oxidative stability test of the coated fiber/tow was performed as in Example 1. A weight retention of 49% was obtained.

Example 14

TGA evaluation of thermo-oxidative protection of SPECTRA® fiber/tows on application of two coatings using a 0.2 M solution of 1 in $CH_2Cl_2$—The weight of the SPECTRA® fiber/tow tested was 0.0148 g. Two coatings of the PCSA polymer was obtained as described in Example 1. The weight of the coating was found to be 0.0045 g (30% by weight of the fiber/tow). The thermo-oxidative stability test of the coated fiber/tow was performed as in Example 1. A weight retention of 60% was obtained.

Example 15

TGA evaluation of thermo-oxidative protection of SPECTRA® fiber/tows on application of three coatings using a 0.2 M solution of 1 in $CH_2Cl_2$—The weight of the SPECTRAL fiber/tow tested was 0.0152 g. Two coatings of the PCSA polymer was obtained as described in Example 1. The weight of the coating was found to be 0.005 g (33% by weight of the fiber/tow). The thermo-oxidative stability test of the coated fiber/tow was performed as in Example 1. A weight retention of 70% was obtained.

Example 16

TGA evaluation of thermo-oxidative protection of VECTRA® fiber/tows on application of a single coating using a 0.2 M solution of 1 in $CH_2Cl_2$—The weight of the VECTRA® fiber/tow tested was 0.0124 g. The procedure for coating with the PCSA solution and the subsequent curing of the ZYLON® fiber/tow is as in Example 1 and the weight of the coating was found to be 0.0025 g (20% by weight of the fiber/tow). The thermo-oxidative stability test of the coated fiber/tow was performed as in Example 1. A weight retention of 43% was obtained.

Example 17

TGA evaluation of thermo-oxidative protection of VECTRA® fiber/tows on application of two coatings using a 0.2 M solution of 1 in $CH_2Cl_2$—The weight of the VECTRA® fiber/tow tested was 0.0138 g. Two coatings of the PCSA polymer was obtained as described in Example 1. The weight of the coating was found to be 0.0035 g (25% by weight of the fiber/tow). The thermo-oxidative stability test of the coated fiber/tow was performed as in Example 1. A weight retention of 58% was obtained.

Example 18

TGA evaluation of thermo-oxidative protection of VECTRA® fiber/tows on application of three coatings using a 0.2 M solution of 1 in $CH_2Cl_2$—The weight of the VECTRA® fiber/tow tested was 0.0135 g. Two coatings of the PCSA polymer was obtained as described in Example 1. The weight of the coating was found to be 0.004 g (30% by weight of the fiber/tow). The thermo-oxidative stability test of the coated fiber/tow was performed as in Example 1. A weight retention of 64% was obtained.

Example 19

TGA evaluation of thermo-oxidative protection of carbon fiber/tows on application of a single coating using a 0.2 M solution of 1 in $CH_2Cl_2$—The weight of the carbon fiber/tow tested was 0.0094 g. The procedure for coating with the PCSA solution and the subsequent curing of the ZYLON® fiber/tow is as in Example 1 and the weight of the coating was found to be 0.001 g (11% by weight of the fiber/tow). The thermo-oxidative stability test of the coated fiber/tow was performed as in Example 1. A weight retention of 78% was obtained.

Example 20

TGA evaluation of thermo-oxidative protection of carbon fiber/tows on application of two coatings using a 0.2 M solution of 1 in $CH_2Cl_2$—The weight of the carbon fiber/tow tested was 0.0098 g. Two coatings of the PCSA polymer was obtained as described in Example 1. The weight of the coating was found to be 0.0015 g (15% by weight of the fiber/tow). The thermo-oxidative stability test of the coated fiber/tow was performed as in Example 1. A weight retention of 89% was obtained.

Example 21

TGA evaluation of thermo-oxidative protection of carbon fiber/tows on application of three coatings using a 0.2 M solution of 1 in $CH_2Cl_2$—The weight of the carbon fiber/tow tested was 0.0092 g. Two coatings of the PCSA polymer was obtained as described in Example 1. The weight of the coating was found to be 0.0017 g (18% by weight of the fiber/tow). The thermo-oxidative stability test of the coated fiber/tow was performed as in Example 1. A weight retention of 92% was obtained.

Example 22

TGA evaluation of thermo-oxidative protection of ZYLON® fiber/tows on application of a 1 M coating solution of a hydrosilated 3+4 C-Ls network polymer—Preparation of the coating solution and coating of the ZYLON® fiber: The hydrosilated carborane-siloxane network coating solution was prepared by thoroughly mixing a mixture of 3 (0.46 g; 1 mmol) and 4 C-Ls (0.18 mL; 0.5 mmol) in a 1½"×1" vial using a mechanical stirrer for 2 min. The mixing was repeated by adding 1 mL of dry hexane to the mixture. At this point a piece of the ZYLON® fiber/tow (0.0251 g) was immersed in the solution and 2 drops of a 2000 ppm Pt Karstedt catalyst (Eq. (17)) solution (prepared by diluting a 0.5 mL portion of a 2.1-2.4% Pt concentration Karstedt catalyst solution in xylene from Gelest, Inc. to 5 mL with xylene) was added to the mixture using a 500 μL syringe and the vigorous mixing was continued for 2 min. The addition of the catalyst solution and the mixing was continued until 10 drops had been added (for a total mixing time of 25 min.) by when the solution had started becoming viscous. At this point the fiber was taken out of the solution and was left to dry in air.

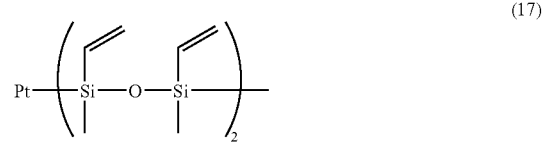

(17)

Curing of the coated ZYLON® fiber: The coated ZYLON® fiber/tow from above was cured at 300° C. under $N_2$ in a TGA instrument for 3 h. The weight of the coating was found to be 0.0065 g (26% by weight of the fiber/tow).

Thermo-oxidative stability test of the hydrosilated 3+4 C-Ls network polymer-coated ZYLON® fiber/tow—Treatment to 1000° C. in air in a TGA instrument: The thermo-oxidative stability test of the coated fiber/tow was performed by heating the sample under air to 1000° C. at 10° C./min in a TGA instrument. A weight retention of 63% was obtained.

Example 23

TGA evaluation of thermo-oxidative protection of KEVLAR® fiber/tows on application of a 1 M coating solution of a hydrosilated 3+4 C-Ls network polymer—The weight of the KEVLAR® fiber/tow tested was 0.0260 g. The preparation of the coating solution, the coating and curing of the fiber with the coating solution and the thermo-oxidative stability test of the coated were done as in Example 22. The weight of the coating was found to be 0.006 g (23% by weight of the fiber/tow). A weight retention of 57% was obtained after the thermo-oxidative test.

Example 24

TGA evaluation of thermo-oxidative protection of ZYLON® fiber/tows on application of a 1 M coating solution of a hydrosilated 4+4 C-Ls network polymer—The weight of the ZYLON® fiber/tow tested was 0.0242 g. The preparation of the coating solution, the coating and curing of the fiber with the coating solution and the thermo-oxidative stability test of the coated were done as in Example 22. In the reaction, 0.455 g (1 mmol) of 1,7-bis(ethynyltetramethyldisiloxyl)m-carborane was used. The weight of the coating was found to be 0.005 g (21% by weight of the fiber/tow). A weight retention of 65% was obtained after the thermo-oxidative test.

Example 25

TGA evaluation of thermo-oxidative protection of KEVLAR® fiber/tows on application of a 1 M coating solution of a hydrosilated 4+4 C-Ls network polymer—The weight of the KEVLAR® fiber/tow tested was 0.0252 g. The preparation of the coating solution, the coating and curing of the fiber with the coating solution and the thermo-oxidative stability test of the coated were done as in Example 22. In the reaction, 0.455 g (1 mmol) of 4 was used. The weight of the coating was found to be 0.0055 g (22% by weight of the fiber/tow). A weight retention of 59% was obtained after the thermo-oxidative test.

Example 26

TGA evaluation of thermo-oxidative protection of ZYLON® fiber/tows on application of a 1 M coating solution of a hydrosilated extended {(3+2 C-Ls)+4 C-Ls} network polymer—Preparation of the Coating Solution (Extended Version) and Coating of the ZYLON® Fiber: the hydrosilated extended vinyl carborane-siloxane network coating solution was prepared by thoroughly mixing a mixture of 3 (0.46 g; 1 mmol) and 2 C-Ls (0.13 mL; 0.5 mmol) in a 1½"×1" vial using a mechanical stirrer for 2 min. To this mixture 1 mL of hexane was added and 3 drops of a 2000 ppm Karstedt catalyst solution in xylene was syringed in using a 500 µL syringe and the mixing was repeated. Then, a 0.09 mL (0.5 mmol) portion of 4 C-Ls was added to this mixture followed by a piece of the ZYLON® fiber/tow (0.0232 g) and 2 drops of a 2000 ppm. Pt Karstedt catalyst solution (using a 500 µL syringe), and the vigorous mixing was continued for 2 min. The addition of the catalyst solution and the mixing was continued until 10 drops had been added (for a total mixing time of 25 min.) by when the solution had started becoming viscous. At this point the fiber was taken out of the solution and was left to dry in air.

Coating and curing: The coating and curing of the fiber with the coating solution and the thermo-oxidative stability test of the coated were done as in Example 22. The weight of the coating was found to be 0.0045 g (20% by weight of the fiber/tow). A weight retention of 61% was obtained after the thermo-oxidative test.

Example 27

TGA evaluation of thermo-oxidative protection of ZYLON® fiber/tows on application of a 1 M coating solution of a hydrosilated 3+3 C-Ls/Me network polymer—The weight of the ZYLON® fiber/tow tested was 0.0228 g. The preparation of the coating solution, the coating and curing of the fiber with the coating solution and the thermo-oxidative stability test of the coated were done as in Example 22 except that 0.21 mL (0.667 mmol) of 3 C-Ls/Me was used in place of 4 C-Ls. The weight of the coating was found to be 0.0055 g (24% by weight of the fiber/tow). A weight retention of 59% was obtained after the thermo-oxidative test.

Example 28

TGA evaluation of thermo-oxidative protection of ZYLON® fiber/tows on application of a 1 M coating solution of a hydrosilated 3+3 C-Ls/Ph network polymer—The weight of the ZYLON® fiber/tow tested was 0.0233 g. The preparation of the coating solution, the coating and curing of the fiber with the coating solution and the thermo-oxidative stability test of the coated were done as in Example 22 except that 0.23 mL (0.667 mmol) of 3 C-Ls/Ph was used in place of 4 C-Ls. The weight of the coating was found to be 0.0055 g (24% by weight of the fiber/tow). A weight retention of 62% was obtained after the thermo-oxidative test.

Example 29

TGA evaluation of thermo-oxidative protection of ZYLON® fiber/tows on application of a 1 M coating solution of a hydrosilated 3+3 C-Ls/Ph network polymer—The weight of the ZYLON® fiber/tow tested was 0.0233 g. The preparation of the coating solution, the coating and curing of the fiber with the coating solution and the thermo-oxidative stability test of the coated were done as in Example 22 except that 0.23 mL (0.667 mmol) of 3 C-Ls/Ph was used in place of 4 C-Ls. The weight of the coating was found to be 0.0055 g (24% by weight of the fiber/tow). A weight retention of 62% was obtained after the thermo-oxidative test.

Example 30

TGA evaluation of thermal protection of ZYLON® fiber/tows under nitrogen on application of a single coating using a 0.2 M solution of 1 in hexane—The weight of the ZYLON® fiber/tow tested was 0.0125 g. 0.456 g of polymer 1 was dissolved in 5 mL of hexane to yield a 0.2 M solution of the material. The procedure for coating with the PCSA solution and the subsequent curing of the ZYLON® fiber/tow is as in Example 1 which was repeated three times and the weight of the coating was found to be 0.003 g (24% by weight of the fiber/tow). The thermo-oxidative stability test of the coated fiber/tow was performed as in Example 1. However, the atmosphere in the TGA instrument was replaced with nitrogen. A weight retention of 88% was obtained.

Example 31

TGA evaluation of thermal protection of ZYLON® fiber/tows under argon on application of a single coating using a 0.2 M solution of 1 in hexane—The weight of the ZYLON® fiber/tow tested was 0.0125 g. 0.456 g of polymer 1 was dissolved in 5 mL of hexane to yield a 0.2 M solution of the material. The procedure for coating with the PCSA solution and the subsequent curing of the ZYLON® fiber/tow is as in Example 1 which was repeated three times and the weight of the coating was found to be 0.003 g (24% by weight of the fiber/tow). The thermo-oxidative stability test of the coated fiber/tow was performed as in Example 1. However, the atmosphere in the TGA instrument was replaced with argon. A weight retention of 90% was obtained.

Example 32

TGA evaluation of thermo-oxidative protection of an optical fiber (with a PVC jacket) on application of a concentrated coating solution of 1—A highly concentrated solution of 1 was obtained in xylene and the optical fiber was immersed in it for 5 minutes. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated optical fiber (with a PVC jacket) results in its catastrophic degradation.

Example 33

TGA evaluation of thermo-oxidative protection of an optical fiber (with a PVC jacket) on application of a concentrated coating solution of 2—A highly concentrated solution of 2 was obtained in xylene and the optical fiber was immersed in it for 5 minutes. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated optical fiber (with a PVC jacket) results in its catastrophic degradation.

Example 34

TGA evaluation of thermo-oxidative protection of an optical fiber (with a PVC jacket) on application of a 1M coating solution of a hydrosilated 3+4 C-Ls network polymer—A 1M hydrosilated coating solution of 3+4 C-Ls/Ph network polymer was prepared as in Example 22. The optical fiber was immersed in it for 5 minutes. This produced a clear coating of the polymer on the optical fiber. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated optical fiber (with a PVC jacket) results in its catastrophic degradation.

Example 35

TGA evaluation of thermo-oxidative protection of an optical fiber (with a polyurethane jacket) on application of a concentrated coating solution of 1—A highly concentrated solution of 1 was obtained in xylene and the optical fiber was immersed in it for 5 minutes. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated optical fiber (with a polyurethane jacket) results in its catastrophic degradation.

Example 36

TGA evaluation of thermo-oxidative protection of an optical fiber (with a polyurethane jacket) on application of a 1 M coating solution of a hydrosilated 3+4 C-Ls network polymer—A 1 M hydrosilated coating solution of 3+4 C-Ls/Ph network polymer was prepared as in Example 22. The optical fiber was immersed in it for 5 minutes. This produced a clear coating of the polymer on the optical fiber. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated optical fiber (with a polyurethane jacket) results in its catastrophic degradation.

Example 37

TGA evaluation of thermo-oxidative protection of a plastic/polymer optical fiber (poly(methylmethacrylate (PMMA) optical fiber (GIPOF)) on application of a concentrated coating solution of 1—A highly concentrated solution of 1 was obtained in xylene and the optical fiber was immersed in it for 5 minutes. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated PMMA optical fiber results in its catastrophic degradation.

Example 38

TGA evaluation of thermo-oxidative protection of a plastic/polymer optical fiber (PMMA optical fiber (GIPOF)) on application of a 1 M coating solution of a hydrosilated (3)+(4 C-Ls) network polymer—A 1 M hydrosilated coating solution of 3+4 C-Ls/Ph network polymer was prepared as in Example 22. The optical fiber was immersed in it for 5 minutes. This produced a clear coating of the polymer on the optical fiber. The coated fiber was cured as in Example 1 and was then heated in a TGA instrument under air to 1000° C. at 10° C./min. On qualitative evaluation, the fiber appeared to have retained most of its weight. In comparison, similar thermo-oxidative treatment of an uncoated PMMA optical fiber results in its catastrophic degradation.

Example 39

TGA evaluation of thermo-oxidative protection of a copper wire on application of a concentrated coating solution of 1—A highly concentrated solution of 1 was obtained in xylene and the optical fiber was immersed in it for 5 minutes. The coated fiber was cured as in Example 1 and was then heated in a TGA instrument under air to 1000° C. at 10° C./min. On qualitative evaluation, the copper wire appeared to have retained most of its weight. In comparison, similar thermo-oxidative treatment of an uncoated copper wire results in its catastrophic oxidation.

Example 40

TGA evaluation of thermo-oxidative protection of a copper wire on application of a concentrated coating solution of 1—A highly concentrated solution of 1 was obtained in xylene and the copper wire was immersed in it for 5 minutes. The coated fiber was cured as in Example 1 and was then heated in a TGA instrument under air to 1000° C. at 10° C./min. On qualitative evaluation, the copper wire appeared to have retained most of its weight. In comparison, similar thermo-oxidative treatment of an uncoated copper wire results in its catastrophic oxidation.

Example 41

Formation of oxidatively stable composites of ZYLON® fibers with 1—ZYLON® fibers were immersed in a concentrated solution of 1 in diethyl ether and were subsequently dried in air. Curing of the coating was performed as in Example 1 and the process of immersion and curing was repeated several times to deposit a thick layer of the material. The coated fibers were then placed in a quartz boat and 1 was added to cover the fibers. The resulting composition was heated to 1000° C. in a flow of nitrogen resulting in the formation of the ceramic-based composite.

Example 42

Formation of oxidatively stable composites of KEVLAR® fibers with 1—KEVLAR® fibers were immersed in a concentrated solution of 1 in diethyl ether and were subsequently dried in air. Curing of the coating was performed as in Example 1 and the process of immersion and curing was repeated several times to deposit a thick layer of the material. The coated fibers were then placed in a quartz boat and 1 was added to cover the fibers. The resulting composition was heated to 1000° C. in a flow of nitrogen resulting in the formation of the ceramic-based composite.

Example 43

Formation of oxidatively stable composites of SPECTRA® fibers with 1—SPECTRA® fibers were immersed in a concentrated solution of 1 in diethyl ether and were subsequently dried in air. Curing of the coating was performed as in Example 1 and the process of immersion and curing was repeated several times to deposit a thick layer of the material. The coated fibers were then placed in a quartz boat and 1 was added to cover the fibers. The resulting composition was heated to 1000° C. in a flow of nitrogen resulting in the formation of the ceramic-based composite.

Example 44

Formation of oxidatively stable composites of ZYLON® fibers with a hydrosilated 3+4 C-Ls network polymer—Several coatings of a hydrosilated 3+4 C-Ls network polymer on ZYLON® fibers were obtained as described in Example 22 after alternating curing cycles. The coated fibers were then placed in a quartz boat and a viscous mixture of a hydrosilated 3+4 C-Ls network polymer in hexane was transferred into the boat. The resulting composition was air dried and subsequently heated to 1000° C. in a flow of nitrogen resulting in the formation of the ceramic-based composite.

Example 45

Comparative tension tests at ambient conditions of thermally treated (at 650° C.) uncoated and 1-coated ZYLON® fiber/tows using a load applying instrument—Three 26" long ZYLON® fiber/tow samples were immersed in a 0.1 M solution of 1 in hexane for 1 min. The samples were air dried along with three 26" long samples of uncoated ZYLON® fiber/tow samples. Each of the coated and the uncoated ZYLON® fiber/tow samples was similarly thermally treated for 1 min each in a region in the flame of a Bunsen burner a temperature of 650° C. (Note: The temperature had been predetermined using a K-type thermocouple). Tension tests were carried out at ambient conditions on the thermally treated coated and uncoated ZYLON® fiber/tow samples using a load applying machine. During the tension test, each of the samples was held in place by a Capstan action grip set and a continually increasing tension was applied on the ZYLON® fiber/tow by gradually increasing the load applied on it. The load at which each of the tested fiber/tow failed was recorded (Table 2). It was observed that, on an average, a thermally treated ZYLON® fiber/tow which had been coated by 1 withstood a load in excess of 130 lbs when compared to an uncoated ZYLON® fiber/tow with a similar thermal treatment history.

TABLE 2

Results of the tensions tests of uncoated and 1-coated ZYLON ® fiber/tow after thermal treatment in air at 650° C. for 1 min

| Sample ID | Load at point of failure (lbs) |
|---|---|
| Uncoated (Sample 1) | 110 |
| Uncoated (Sample 2) | 140 |
| Uncoated (Sample 3) | 130 |
| 1-coated (Sample 1) | 280 |
| 1-coated (Sample 2) | 260 |
| 1-coated (Sample 3) | 320+ |

Example 46

Comparative tension tests at ambient conditions of thermally treated (at 700° C.) uncoated and 1-coated ZYLON® fiber/tows using a load applying instrument—Three 26" long ZYLON® fiber/tow samples were immersed in a 0.1 M solution of 1 in hexane for 1 min. The samples were air dried along with three 26" long samples of uncoated ZYLON® fiber/tow samples. The thermal treatment was performed at 700° C. for a minute and the tension tests were performed as in Example 45. The results are provided in Table 3. It was observed that, on an average, a thermally treated ZYLON® fiber/tow which had been coated by 1 withstood a load in excess of 80 lbs when compared to an uncoated ZYLON® fiber/tow with a similar thermal treatment history.

TABLE 3

Results of the tensions tests of uncoated and 1-coated ZYLON ® fiber/tow after thermal treatment in air at 650° C. for 1 min

| Sample ID | Load at point of failure (lbs) |
|---|---|
| Uncoated (Sample 1) | 30 |
| Uncoated (Sample 2) | 25 |
| Uncoated (Sample 3) | 35 |
| 1-coated (Sample 1) | 110 |
| 1-coated (Sample 2) | 105 |
| 1-coated (Sample 3) | 115 |

Example 47

Comparative determinations of 'time to failure' values at elevated temperature (650° C.) of uncoated and 1-coated ZYLON® fiber/tows under a constant applied load of 58 lbs (Coating performed by the immersion for 2 minutes of the ZYLON® fiber/tow in a 0.2 M solution of 1 in hexane)—Three 12" long ZYLON® fiber/tow samples were immersed in a 0.2 M solution of 1 in hexane for 2 min. The samples were air and vacuum dried along with three 12" long samples of uncoated ZYLON® fiber/tow samples to remove the coating solvent. The 'time to failure' tests of the fibers were performed in an instrument with the capability to simultaneously apply a constant load and a constant blast of hot air at a predetermined temperature on the tested fiber. The time at which the fiber failed during the test was determined. The results are described in Table 4. The average 'time to failure' value of the uncoated fiber/tow samples is 94 sec and that of the 1-coated samples is 176 sec. This represents an 87% improvement in 'time to failure' value on application of the coating.

TABLE 4

Results from the 'time to failure' value tests of uncoated and 1-coated ZYLON ® fiber/tow

| Sample ID | 'time to failure' (sec) |
| --- | --- |
| Uncoated (Sample 1) | 107 |
| Uncoated (Sample 2) | 85 |
| Uncoated (Sample 3) | 90 |
| 1-coated (Sample 1) | 200 |
| 1-coated (Sample 2) | 138 |
| 1-coated (Sample 3) | 190 |

Example 48

Comparative determinations of 'time to failure' values at elevated temperature (650° C.) of uncoated and 1-coated ZYLON® fiber/tows under a constant applied load of 58 lbs (Coating performed by the immersion for 30 minutes of the ZYLON® fiber/tow in a 0.2 M solution of 1 in hexane)— Three 12" long ZYLON® fiber/tow samples were immersed in a 0.2 M solution of 1 in hexane for 30 min. The samples were air and vacuum dried along with three 12" long samples of uncoated ZYLON® fiber/tow samples to remove the coating solvent. The 'tinge to failure' tests of the fibers were performed as in Example 47. The results are described in Table 5. The average 'time to failure' value of the uncoated fiber/tow samples is 70 sec and that of the 1-coated samples is 135 sec. This represents a 93% improvement in the 'time to failure' value on application of the coating.

TABLE 5

Results from the 'time to failure' value tests of uncoated and 1-coated ZYLON ® fiber/tow

| Sample ID | 'time to failure' (sec) |
| --- | --- |
| Uncoated (Sample 1) | 71 |
| Uncoated (Sample 2) | 66 |
| Uncoated (Sample 3) | 73 |
| 1-coated (Sample 1) | 130 |
| 1-coated (Sample 2) | 135 |
| 1-coated (Sample 3) | 140 |

Example 49

Comparative determinations of 'time to failure' values at elevated temperature (650° C.) of uncoated and 1-coated ZYLON® fiber/tows under a constant applied load of 58 lbs (Coating performed by the immersion for 30 minutes of the ZYLON® fiber/tow in a 0.4 M solution of 1 in hexane)— Three 12" long ZYLON® fiber/tow samples were immersed in a 0.4 M solution of 1 in hexane for 30 min. The samples were air and vacuum dried along with three 12" long samples of uncoated ZYLON® fiber/tow samples to remove the coating solvent. The 'time to failure' tests of the fibers were performed as in Example 47. The results are described in Table 6. The 'time to failure' values are found to scattered for the 1-coated samples. This is believed to be due to some detrimental effects of the coating on the thermo-oxidative stability of the fiber once an optimum coating thickness/amount is exceeded.

TABLE 6

Results from the 'time to failure' value tests of uncoated and 1-coated ZYLON ® fiber/tow

| Sample ID | 'time to failure' (sec) |
| --- | --- |
| Uncoated (Sample 1) | 80 |
| Uncoated (Sample 2) | 55 |
| Uncoated (Sample 3) | 70 |
| 1-coated (Sample 1) | 19 |
| 1-coated (Sample 2) | 135 |
| 1-coated (Sample 3) | 165 |

Example 50

Comparative determinations of 'time to failure' values at elevated temperature (650° C.) of uncoated and 1-coated carbon fiber/tows under a constant applied load of 58 lbs (Coating performed by the immersion for 30 minutes of the carbon fiber/tow in a 0.2 M solution of 1 in hexane)—Three 12" long carbon fiber/tow samples were immersed in a 0.2 M solution of 1 in hexane for 30 min. The samples were air and vacuum dried along with three 12" long samples of uncoated carbon fiber/tow samples to remove the coating solvent. The 'time to failure' tests of the fibers were performed as in Example 47. The time at which the fiber failed during the test was determined. The results are described in Table 7. The average 'time to failure' value of the uncoated fiber/tow samples is 445 sec and that of the 1-coated samples is 715 sec. This represents a 61% improvement in 'time to failure' value on application of the coating.

TABLE 7

Results from the 'time to failure' value tests of uncoated and 1-coated carbon fiber/tow

| Sample ID | 'time to failure' (sec) |
| --- | --- |
| Uncoated (Sample 1) | 420 |
| Uncoated (Sample 2) | 460 |
| Uncoated (Sample 3) | 455 |
| 1-coated (Sample 1) | 511 |
| 1-coated (Sample 2) | 985 |
| 1-coated (Sample 3) | 650 |

Example 51

Comparative determinations of 'time to failure' values at elevated temperature (650° C.) of uncoated and 1-coated carbon fiber/tows under a constant applied load of 58 lbs (Coating performed by the immersion for 30 minutes of the carbon fiber/tow in a 0.4 M solution of 1 in hexane)—Three 12" long carbon fiber/tow samples were immersed in a 0.2 M solution of 1 in hexane for 30 min. The samples were air and vacuum dried along with three 12" long samples of uncoated carbon fiber/tow samples to remove the coating solvent. The 'time to failure' tests of the fibers were performed as in Example 47. The time at which the fiber failed during the test was determined. The results are described in Table 8. The average 'time to failure' value of the uncoated fiber/tow samples is 333 sec and that of the 1-coated samples is 623 sec. This represents an 87% improvement in 'time to failure' value on application of the coating.

TABLE 8

Results from the 'time to failure' value tests of uncoated and 1-coated carbon fiber/tow

| Sample ID | 'time to failure' (sec) |
| --- | --- |
| Uncoated (Sample 1) | 440 |
| Uncoated (Sample 2) | 290 |
| Uncoated (Sample 3) | 270 |
| 1-coated (Sample 1) | 675 |
| 1-coated (Sample 2) | 625 |
| 1-coated (Sample 3) | 570 |

Example 52

Comparative determinations of 'time to failure' values at elevated temperature (650° C.) of uncoated and 1-coated KEVLAR® fiber/tows under a constant applied load of 58 lbs (Coating performed by the immersion for 30 minutes of the KEVLAR® fiber/tow in a 0.2 M solution of 1 in hexane)—Three 12" long KEVLAR® fiber/tow samples were immersed in a 0.2 M solution of 1 in hexane for 30 min. The samples were air and vacuum dried along with three 12" long samples of uncoated KEVLAR® fiber/tow samples to remove the coating solvent. The 'time to failure' tests of the fibers were performed as in Example 47. The time at which the fiber failed during the test was determined. The results are described in Table 9. The average 'time to failure' value of the uncoated fiber/tow samples is 19 sec and that of the 1-coated samples is 40 sec. This represents a 110% improvement in 'time to failure' value on application of the coating.

TABLE 9

Results from the 'time to failure' value tests of uncoated and 1-coated KEVLAR ® fiber/tow

| Sample ID | 'time to failure' (sec) |
| --- | --- |
| Uncoated (Sample 1) | 20 |
| Uncoated (Sample 2) | 18 |
| Uncoated (Sample 3) | 19 |
| 1-coated (Sample 1) | 40 |
| 1-coated (Sample 2) | 42 |
| 1-coated (Sample 3) | 39 |

Example 53

Comparative determinations of 'time to failure' values at elevated temperature (650° C.) of uncoated and the hydrosilated 3+4 C-Ls network polymer-coated ZYLON® fiber/tows under a constant applied load of 58 lbs—Three 12" long ZYLON® fiber/tow samples were immersed in a 1 M solution of the hydrosilated 3+4 C-Ls network polymer in hexane for 30 min. The samples were air and vacuum dried along with three 12" long samples of uncoated ZYLON® fiber/tow samples to remove the coating solvent. The 'time to failure' tests of the fibers were performed in an instrument with the capability to simultaneously apply a constant load and a constant blast of hot air at a predetermined temperature on the tested fiber. The time at which the fiber failed during the test was determined. The results are described in Table 10. The average 'time to failure' value of the uncoated fiber/tow samples is 87 sec and that of the hydrosilated 3+4 C-Ls network polymer-coated samples is 141 sec. This represents a 62% improvement in 'time to failure' value on application of the coating.

TABLE 10

Results from the 'time to failure' value tests of uncoated and the hydrosilated 3 + 4 C-Ls network polymer-coated ZYLON ® fiber/tow

| Sample ID | 'time to failure' (sec) |
| --- | --- |
| Uncoated (Sample 1) | 89 |
| Uncoated (Sample 2) | 82 |
| Uncoated (Sample 3) | 90 |
| 3 + 4 C-Ls-coated (Sample 1) | 140 |
| 3 + 4 C-Ls-coated (Sample 2) | 135 |
| 3 + 4 C-Ls-coated (Sample 3) | 148 |

Example 54

Preparation of the coating mixture and coating solution containing a surfactant using the linear PCSA polymers—1 g (2.2 mmol) of polymer 1 or 1.33 g of polymer 5 was sonicated with 0.3 g of the silicone surfactant DC 190 or DC 193 (FIG. 4) for 6 h. This yielded a 30% by weight solution of the silicone surfactant with the PCSA polymer. (Note: Instead of DC 190 or DC 193, any of the silicone surfactant from FIGS. 4 and 5 can be used for the coating mixture production). The well-mixed mixture was dissolved in 100 mL of distilled water to yield a 0.022 M (in PCSA) coating solution mixture. The mixture was observed to disperse well and stay dissolved during the initial half an hour after which coagulation and precipitation of the mixture occurs slowly. Hence, best results of coating applications utilizing this solution may be achieved during this period.

Example 55

Preparation of the coating mixture and coating solution containing a surfactant using the cross-linked carboranylenesiloxane network polymers—1 g (2.2 mmol) of the divinyl monomer 3 or 1 g (2.2 mmol) of the diethynyl monomer 4 was mixed well with 0.37 g or 0.41 mL (1.1 mmol) of tetrakis (dimethylsiloxy)silane 4 C-Ls in 0.5 mL of hexane. To this mixture 1 drop of a 2.4 wt % Pt Karstedt catalyst (Eq. (17)) solution was added and the mixture was mixed well. At this point, any residual hexane in the crosslinked mixture was removed. To form the coating formulation, this mixture was treated with 0.3 g of DC 190 or DC 193 which was followed by sonication for 6 h. (Note: Instead of DC 190 or DC 193, any of the silicone surfactant from FIGS. 4 and 5 can be used for the coating mixture production). The well-mixed mixture was dissolved in 100 mL of distilled water to yield a 0.022 M (in the hydrosilated carboranylenesiloxane network) coating solution mixture. The mixture was observed to disperse well and stay dissolved during the initial hour after which coagulation and precipitation of the mixture occurs slowly. Hence, the best results for a coating run utilizing this solution may be achieved during this period.

Example 56

Coating of ZYLON® fibers using the PCSA/DC 193 coating formulation from Example 54—Pieces of ~½ to 1 inch ZYLON® fiber samples were severed from a spool of ZYLON® fiber. The pieces were left immersed in the solution from Example 54 for durations of 5 min, 10 min, and 30 min respectively. After the immersion, the fibers were drawn out of the solution and were air dried.

Example 57

Thermo-oxidative stability test of the coated ZYLON® fiber from Example 56—A 5 min-immersed ZYLON® fiber sample was placed in a platinum pan in an atmosphere of air in a TGA instrument. The air flow was maintained at 100 cc/min throughout the experiment. The sample was heated to 710° C. at 60° C./min and was held at that temperature for 30 min. For comparison, an uncoated ZYLON® fiber sample severed from the same spool that was used in the experiment was subjected to a similar thermo-oxidative treatment for 30 min. Analysis of the TGA thermograms revealed that the PCSA/DC 193-coated ZYLON® fiber retained 51% of its initial mass in comparison to the uncoated ZYLON® fiber which retained only 21% of its initial mass after 22 min at 710° C.

Example 58

Thermo-oxidative stability test of the coated ZYLON® fiber from Example 56—A 10 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 57. Analysis of the TGA thermograms revealed that the PCSA/DC 193-coated ZYLON® fiber retained 58% of its initial mass in comparison to the uncoated ZYLON® fiber which retained only 21% of its initial mass after 2½ min at 710° C.

Example 59

Thermo-oxidative stability test of the coated ZYLON® fiber from Example 56—A 30 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 57. Analysis of the TGA thermograms revealed that the PCSA/DC 193-coated ZYLON® fiber retained 62% of its initial mass in comparison to the uncoated ZYLON® fiber which retained only 21% of its initial mass after 2½ min at 710° C.

Example 60

Coating of carbon fibers using the PCSA/DC 193 coating formulation from Example 54—Pieces of ½-1 inch carbon fiber samples were severed from a spool of carbon fiber cable tows. The pieces were left immersed in the solution from Example 54 for durations of 5 min, 10 min, and 30 min respectively. After the immersion, the fibers were drawn out of the solution and were air dried.

Example 61

Thermo-oxidative stability test of the coated carbon fiber from Example 60—A 5 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 50% of its initial mass in comparison to 1% at 800° C. for the uncoated carbon fiber cable tows.

Example 62

Thermo-oxidative stability test of the coated carbon fiber from Example 60—A 10 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 57% of its initial mass in comparison to 1% at 800° C. for the uncoated carbon fiber cable tows.

Example 63

Thermo-oxidative stability test of the coated carbon fiber from Example 60—A 30 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 60% of its initial mass in comparison to 1% at 800° C. for the uncoated carbon fiber cable tows.

Example 64

Coating of KEVLAR® fibers using the PCSA/DC 193 coating formulation from Example 54—Pieces of ~½ to 1 inch KEVLAR® fiber samples were severed from a spool of KEVLAR® fiber cable tows. The pieces were left immersed in the solution from Example 54 for durations of 5 min, 10 min, and 30 min respectively. After the immersion, the fibers were drawn out of the solution and were air dried.

Example 65

Thermo-oxidative stability test of the coated KEVLAR® fiber from Example 64—A 5 min-immersed KEVLAR® fiber sample was placed in a platinum pan in an atmosphere of air in a TGA instrument. The air flow was maintained at 100 cc/min throughout the experiment. The sample was heated to 550° C. at 60° C./min and was held at that temperature for 30 min. For comparison, an uncoated KEVLAR® fiber sample severed from the same spool that was used in the experiment was subjected to a similar thermo-oxidative treatment for 30 min. Analysis of the TGA thermograms revealed that the PCSA/DC 193-coated KEVLAR® fiber retained 55% of its initial mass in comparison to the uncoated KEVLAR® fiber which retained only 19% of its initial mass after 2½ min at 550° C.

Example 66

Thermo-oxidative stability test of the coated KEVLAR® fiber from Example 64—A 10 min-immersed KEVLAR® fiber sample was placed in a platinum pan in an atmosphere of air in a TGA instrument. The air flow was maintained at 100 cc/min throughout the experiment. The thermo-oxidative tests of the coated and uncoated fibers to 550° C. at 60° C./min were performed as in Example 65. Analysis of the TGA thermograms revealed that the PCSA/DC 193-coated KEVLAR® fiber retained 61% of its initial mass in comparison to the uncoated KEVLAR® fiber which retained only 19% of its initial mass after 22 min at 550° C.

Example 67

Thermo-oxidative stability test of the coated KEVLAR® fiber from Example 64—A 30 min-immersed KEVLAR® fiber sample was placed in a platinum pan in an atmosphere of air in a TGA instrument. The air flow was maintained at 100 cc/min throughout the experiment. The thermo-oxidative tests of the coated and uncoated fibers to 550° C. at 60° C./min were performed as in Example 65. Analysis of the TGA thermograms revealed that the PCSA/DC 193-coated KEVLAR® fiber retained 68% of its initial mass in comparison to the uncoated KEVLAR® fiber which retained only 19% of its initial mass after 22 min at 550° C.

Note: Similar thermo-oxidative protection can also be afforded to high performance organic fibers such as VECTRA® and SPECTRA® as observed in the cases of their coating studies with PCSA polymer in a hexane solvent.

Example 68

Coating of ZYLON® fibers using the crosslinked-network carboranylenesiloxane/DC 193 coating formulation (from Example 55)—Pieces of ~½ to 1 inch ZYLON® fiber samples were severed from a spool of ZYLON® fiber. The pieces were left immersed in the solution from Example 55 for durations of 5 min, 10 min, and 30 min respectively. After the immersion, the fibers were drawn out of the solution and were air dried.

Example 69

Thermo-oxidative stability test of the coated ZYLON® fiber from Example 68—A 5 min-immersed ZYLON® fiber sample was placed in a platinum pan in an atmosphere of air in a TGA instrument. The air flow was maintained at 100 cc/min throughout the experiment. The sample was heated to 710° C. at 60° C./min and was held at that temperature for 30 min. For comparison, an uncoated ZYLON® fiber sample severed from the same spool that was used in the experiment was subjected to a similar thermo-oxidative treatment for 30 min. Analysis of the TGA thermograms revealed that the crosslinked-network carboranylenesiloxane/DC 193-coated ZYLON® fiber retained 47% of its initial mass in comparison to the uncoated ZYLON® fiber which retained only 21% of its initial mass after 22 min at 710° C.

Example 70

Thermo-oxidative stability test of the coated ZYLON® fiber from Example 68—A 10 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 69. Analysis of the TGA thermograms revealed that the crosslinked-network carboranylenesiloxane/DC 193-coated ZYLON® fiber retained 53% of its initial mass in comparison to the uncoated ZYLON® fiber which retained only 210% of its initial mass after 2½ min at 710° C.

Example 71

Thermo-oxidative stability test of the coated ZYLON® fiber from Example 68—A 30 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 69. Analysis of the TGA thermograms revealed that the crosslinked-network carboranylenesiloxane/DC 193-coated ZYLON® fiber retained 58% of its initial mass in comparison to the uncoated ZYLON® fiber which retained only 21% of its initial mass after 22 min at 710° C.

Example 72

Coating of carbon fibers using the crosslinked-network carboranylenesiloxane/DC 193 coating formulation (from Example 55)—Pieces of ~½-1 inch carbon fiber samples were severed from a spool of Carbon fiber cable tows. The pieces were left immersed in the solution from Example 55 for durations of 5 min, 10 min, and 30 min respectively. After the immersion, the fibers were drawn out of the solution and were air dried.

Example 73

Thermo-oxidative stability test of the coated carbon fiber from Example 72—A 5 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the crosslinked-network carboranylenesiloxane/DC 193-coated carbon fiber cable tows retained 45% of its initial mass in comparison to 1% at 800° C. for the uncoated carbon fiber cable tows.

Example 74

Thermo-oxidative stability test of the coated carbon fiber from Example 72—A 10 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the crosslinked-network carboranylenesiloxane/DC 193-coated carbon fiber cable tows retained 51% of its initial mass in comparison to 1% at 800° C. for the uncoated carbon fiber cable tows.

Example 75

Thermo-oxidative stability test of the coated carbon fiber from Example 72—A 30 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the crosslinked-network carboranylenesiloxane/DC 193-coated carbon fiber cable tows retained 55% of its initial mass in comparison to 1% at 800° C. for the uncoated carbon fiber cable tows.

Example 76

Coating of KEVLAR® fibers using the crosslinked-network carboranylenesiloxane/DC 193 coating formulation (from Example 55)—Pieces of ~½ to 1 inch KEVLAR® fiber samples were severed from a spool of KEVLAR® fiber. The pieces were left immersed in the solution from Example 55 for durations of 5 min, 10 min, and 30 min respectively. After the immersion, the fibers were drawn out of the solution and were air dried.

Example 77

Thermo-oxidative stability test of the coated KEVLAR® fiber from Example 76—A 5 min-immersed KEVLAR® fiber sample was placed in a platinum pan in an atmosphere of air in a TGA instrument. The air flow was maintained at 100 cc/min throughout the experiment. The sample was heated to 550° C. at 60° C./min and was held at that temperature for 30 min. For comparison, an uncoated KEVLAR® fiber sample severed from the same spool that was used in the experiment was subjected to a similar thermo-oxidative treatment for 30 min. Analysis of the TGA thermograms revealed that the crosslinked-network carboranylenesiloxane/DC 193-coated KEVLAR® fiber retained 46% of its initial mass in comparison to the uncoated KEVLAR® fiber which retained only 19% of its initial mass after 22 min at 550° C.

Example 78

Thermo-oxidative stability test of the coated KEVLAR® fiber from Example 76—A 10 min-immersed KEVLAR® fiber sample was placed in a platinum pan in an atmosphere of air in a TGA instrument. The air flow was maintained at 100 cc/min throughout the experiment. The thermo-oxidative tests of the coated and uncoated fibers to 550° C. at 60° C./min were performed as in Example 24. Analysis of the TGA thermograms revealed that the crosslinked-network carboranylenesiloxane/DC 193-coated KEVLAR® fiber retained 52% of its initial mass in comparison to the uncoated KEVLAR® fiber which retained only 19% of its initial mass after 2½ min at 550° C.

Example 79

Thermo-oxidative stability test of the coated KEVLAR® fiber from Example 76—A 30 min-immersed KEVLAR® fiber sample was placed in a platinum pan in an atmosphere of air in a TGA instrument. The air flow was maintained at 100 cc/min throughout the experiment. The thermo-oxidative tests of the coated and uncoated fibers to 550° C. at 60° C./min were performed as in Example 24. Analysis of the TGA thermograms revealed that the crosslinked-network carboranylenesiloxane/DC 193-coated KEVLAR® fiber retained 59% of its initial mass in comparison to the uncoated KEVLAR® fiber which retained only 19% of its initial mass after 2½ mix at 550° C.

Note: Similar thermo-oxidative protection can also be afforded to high performance organic fibers such as VECTRA® and SPECTRA® as observed in the cases of their coating studies with crosslinked carboranylenesiloxane network polymer in a hexane solvent.

Example 80

Preparation of the coating mixture and coating solution containing a surfactant using the linear PCSA polymers—1 g (2.2 mmol) of polymer 1 or 1.33 g (2.2 mmol) of polymer 5 was sonicated with 0.5 g of the silicone surfactant DC 190 or DC 193 for 6 h. This yielded a 50% by weight solution of the silicone surfactant with the PCSA polymer. (Note: Instead of DC 190 or DC 193, any of the silicone surfactant from FIGS. 4 and 5 can be used for the coating mixture production). The well-mixed mixture was dissolved in 100 mL of distilled water to yield a 0.022 M (in PCSA) coating solution mixture. The mixture was observed to disperse well and stay dissolved during the initial hour after which coagulation and precipitation of the mixture occurs slowly. Hence, best results of coating applications utilizing this solution may be achieved during this period.

Example 81

Preparation of the coating mixture and coating solution containing a surfactant using the linear PCSA polymers—1 g (2.2 mmol) of polymer 1 or 1.33 g (2.2 mmol) of polymer 5 was sonicated with 0.75 g of the silicone surfactant DC 190 or DC 193 for 6 h. This yielded a 75% by weight solution of the silicone surfactant with the PCSA polymer. (Note: Instead of DC 190 or DC 193, any of the silicone surfactant from FIGS. 4 and 5 can be used for the coating mixture production). The well-mixed mixture was dissolved in 100 mL of distilled water to yield a 0.022 M (in PCSA) coating solution mixture. The mixture was observed to disperse well and stay dissolved for up to 4 hours after which coagulation and precipitation of the mixture occurs slowly. Hence, best results of coating applications utilizing this solution may be achieved during this period.

Example 82

Coating of ZYLON® fibers using the PCSA/DC 193 coating formulation in Example 80—Pieces of ~½ to 1 inch ZYLON® fiber samples were severed from a spool of ZYLON® fiber. The pieces were left immersed in the solution from Example 80 for durations of 5 min, 10 min, and 30 min respectively. After the immersion, the fibers were drawn out of the solution and were air dried.

Example 83

Thermo-oxidative stability test of the coated ZYLON® fiber from Example 82—A 5 min-immersed ZYLON® fiber sample was placed in a platinum pan in an atmosphere of air in a TGA instrument. The air flow was maintained at 100 cc/min throughout the experiment. The sample was heated to 710° C. at 60° C./min and was held at that temperature for 30 min. For comparison, an uncoated ZYLON® fiber sample severed from the same spool that was used in the experiment was subjected to a similar thermo-oxidative treatment for 30 min. Analysis of the TGA thermograms revealed that the PCSA/DC 193-coated ZYLON® fiber retained 29% of its initial mass in comparison to the uncoated ZYLON® fiber which retained only 21% of its initial mass after 2½ min at 710° C.

Example 84

Thermo-oxidative stability test of the coated ZYLON® fiber from Example 82—A 10 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 83. Analysis of the TGA thermograms revealed that the PCSA/DC 193-coated ZYLON® fiber retained 32% of its initial mass in comparison to the uncoated ZYLON® fiber which retained only 21% of its initial mass after 22 min at 710° C.

Example 85

Thermo-oxidative stability test of the coated ZYLON® fiber from Example 82—A 30 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 83. Analysis of the TGA thermograms revealed that the PCSA/DC 193-coated ZYLON® fiber retained 34% of its initial mass in comparison to the uncoated ZYLON® fiber which retained only 21% of its initial mass after 2½ min at 710° C.

Example 86

Coating of carbon fibers using the PCSA/DC 193 coating formulation in Example 80—Pieces of ~½-1 inch carbon fiber samples were severed from a spool of carbon fiber cable tows. The pieces were left immersed in the solution from Example 80 for durations of 5 min, 10 min, and 30 min respectively. After the immersion, the fibers were drawn out of the solution and were air dried.

Example 87

Thermo-oxidative stability test of the coated carbon fiber from Example 86—A 5 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 29% of its initial mass in comparison to 1% at 800° C. for the uncoated carbon fiber cable tows.

Example 88

Thermo-oxidative stability test of the coated carbon fiber from Example 86—A 10 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 32% of its initial mass in comparison to 1% at 800° C. for the uncoated carbon fiber cable tows.

Example 89

Thermo-oxidative stability test of the coated carbon fiber from Example 86—A 30 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 35% of its initial mass in comparison to 1% at 800° C. for the uncoated carbon fiber cable tows.

Example 90

Coating of ZYLON® fibers using the PCSA/DC 193 coating formulation in Example 81—Pieces of ~½ to 1 inch ZYLON® fiber samples were severed from a spool of ZYLON® fiber. The pieces were left immersed in the solution from Example 81 for durations of 5 min, 10 min, and 30 min respectively. After the immersion, the fibers were drawn out of the solution and were air dried.

Example 91

Thermo-oxidative stability test of the coated ZYLON® fiber from Example 90—A 5 min-immersed ZYLON® fiber sample was placed in a platinum pan in an atmosphere of air in a TGA instrument. The air flow was maintained at 100 cc/min throughout the experiment. The sample was heated to 710° C. at 60° C./min and was held at that temperature for 30 min. For comparison, an uncoated ZYLON® fiber sample severed from the same spool that was used in the experiment was subjected to a similar thermo-oxidative treatment for 30 min. Analysis of the TGA thermograms revealed that the PCSA/DC 193-coated ZYLON® fiber retained 26% of its initial mass in comparison to the uncoated ZYLON® fiber which retained only 21% of its initial mass after 2½ min at 710° C.

Example 92

Thermo-oxidative stability test of the coated ZYLON® fiber from Example 90—A 10 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 91. Analysis of the TGA thermograms revealed that the PCSA/DC 193-coated ZYLON® fiber retained 30% of its initial mass in comparison to the uncoated ZYLON® fiber which retained only 21% of its initial mass after 22 min at 710° C.

Example 93

Thermo-oxidative stability test of the coated ZYLON® fiber from Example 90—A 30 min-immersed ZYLON® fiber sample was placed in a platinum pan in an atmosphere of air in a TGA instrument. The air flow was maintained at 100 cc/min throughout the experiment. The thermo-oxidative tests of the coated and uncoated fibers to 710° C. at 60° C./min were performed as in Example 91. Analysis of the TGA thermograms revealed that the PCSA/DC 193-coated ZYLON® fiber retained 32% of its initial mass in comparison to the uncoated ZYLON® fiber which retained only 21% of its initial mass after 22 min at 710° C.

Example 94

Coating of carbon fibers using the PCSA/DC 193 coating formulation in Example 81—Pieces of ~½-1 inch carbon fiber samples were severed from a spool of Carbon fiber cable tows. The pieces were left immersed in the solution from Example 81 for durations of 5 min, 10 min, and 30 min respectively. After the immersion, the fibers were drawn out of the solution and were air dried.

Example 95

Thermo-oxidative stability test of the coated carbon fiber from Example 94—A 5 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 27% of its initial mass in comparison to 1% at 800° C. for the uncoated carbon fiber cable tows.

Example 96

Thermo-oxidative stability test of the coated carbon fiber from Example 94—A 10 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 30% of its initial mass in comparison to 1% at 800° C. for the uncoated carbon fiber cable tows.

Example 97

Thermo-oxidative stability test of the coated carbon fiber from Example 94—A 30 min-immersed carbon fiber sample was placed in a platinum pan in an atmosphere of air in a TGA instrument. The air flow was maintained at 100 cc/min throughout the experiment. The sample was heated to 1000° C. at 10° C./min. For comparison, an uncoated carbon fiber sample severed from the same spool that was used in the experiment was subjected to a similar thermo-oxidative treatment. Analysis of the TGA thermograms revealed that the PCSA/DC 193-coated carbon fiber cable tows retained 33% of its initial mass in comparison to 1% at 800° C. for the uncoated carbon fiber cable tows.

Many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A coated fiber comprising:
   a fiber comprising a linear polymer; and
   a coating on the fiber comprising a siloxane-carborane polymer or a thermoset or ceramic made therefrom;
      wherein the linear polymer comprises poly(p-phenylene-2,6-benzobisoxazole), poly(p-phenylene terephthalamide), high molecular weight polyethylene, poly(4-oxybenzoate-co-2,6-oxynaphthoate), polyethylene terephthalate, or poly(pyridobisimidazole-2,6-diyl-(2,5-dihydroxy-p-phenylene)).

2. The coated fiber of claim 1, wherein the siloxane-carborane polymer has the formula:

$\{C\equiv C-C\equiv C-(SiR_2-O)_m-SiR_2-[CB_{10}H_{10}C-SiR_2-(O-SiR_2)_m]_p\}_n-;$ wherein each R is an independently selected organic group; and
   wherein each m, each p, and n are independently selected positive integers.

3. The coated fiber of claim 2, wherein each R is methyl, each m is 1, 2, or 3, and each p is 1 or 2.

4. The coated fiber of claim 2, wherein each p is greater than or equal to 2.

5. The coated fiber of claim 1, wherein the siloxane-carborane polymer or thermoset or ceramic made therefrom is made from a hydrosilation reaction of a siloxane-carborane compound containing at least two unsaturated carbon-carbon bonds and a silane compound.

6. The coated fiber of claim 5;
   wherein the siloxane-carborane compound has the formula:

$U-(SiR_2-O)_m-SiR_2-CB_{10}H_{10}C-SiR_2-(O-SiR_2)_m-U;$ and wherein the silane compound has the formula:

$H-SiR_2-(O-SiR^1R^2)_n-O-SiR_2-H;$ wherein each R is an independently selected organic group;
   wherein each $R^1$ is independently selected from H, R, methyl, phenyl, and $-O-SiR_2-H$;
   wherein each $R^2$ is independently selected from H, R, methyl, and $-O-SiR_2-H$;
   wherein each U is an independently selected group containing an unsaturated carbon-carbon bond; and
   wherein each m and n is an independently selected positive integer.

7. The coated fiber of claim 6, wherein each R is methyl, each m is 1, and each U is vinyl or ethynyl.

8. The coated fiber of claim 6, wherein the silane compound is tetrakis(dimethylsiloxyl)silane, methyltris(dimethylsiloxyl)silane, phenyltris(dimethylsiloxyl)silane, or 1,1,3,3,5,5-hexamethyltrisiloxane.

9. The coated fiber of claim 1, wherein the coating comprises a surfactant containing silicon.

10. The coated fiber of claim 9, wherein the surfactant is: $Si(CH_3)_3-O-[Si(CH_3)_2-O]_x-[SiR^3(CH_3)-O]_y-Si(CH_3)_3$;
    wherein $R^3$ is:
    $-CH_2-CH_2-CH_2-(O-CH_2-CH_2)_q-(O-CH_2CH_2-CH_2)_r-O-CO-CH_3$ or $-(O-CH_2-CH_2)_q-O-CO-CH_3$;
    wherein r, q, x, and y are average numbers of the respective repeat units.

11. A coated fiber comprising:
an organic fiber; and
a coating on the organic fiber comprising a siloxane-carborane polymer or a thermoset or ceramic made therefrom and a surfactant.

12. The coated fiber of claim 11;
wherein the siloxane-carborane compound has the formula:

U—(SiR$_2$—O)$_m$—SiR$_2$—CB$_{10}$H$_{10}$C—SiR$_2$—(O—SiR$_2$)$_m$—U; and wherein the silane compound has the formula:

H—SiR$_2$—(O—SiR$^1$R$^2$)$_n$—O—SiR$_2$—H;

wherein each R is an independently selected organic group;
wherein each R$^1$ is independently selected from H, R, methyl, phenyl, and —O—SiR$_2$—H;
wherein each R$^2$ is independently selected from H, R, methyl, and —O—SiR$_2$—H;
wherein each U is an independently selected group containing an unsaturated carbon-carbon bond; and
wherein each m and n is an independently selected positive integer.

13. The coated fiber of claim 12, wherein each R is methyl, each m is 1, and each U is vinyl or ethynyl.

14. The coated fiber of claim 12, wherein the silane compound is tetrakis(dimethylsiloxyl)silane, methyltris(dimethylsiloxyl)silane, phenyltris(dimethylsiloxyl)silane, or 1,1,3,3,5,5-hexamethyltrisiloxane.

15. The coated fiber of claim 11;
wherein the siloxane-carborane polymer has the formula:

{C≡C—C≡C—(SiR$_2$—O)$_m$SiR$_2$—[CB$_{10}$H$_{10}$C—SiR$_2$—(O—SiR$_2$)$_m$]$_p$}$_n$—;

wherein each R is an independently selected organic group; and
wherein each m, each p, and n are independently selected positive integers; and
wherein the coating comprises the surfactant.

16. The coated fiber of claim 15, wherein each R is methyl, each m is 1, 2, or 3, and each p is 1 or 2.

17. The coated fiber of claim 11, wherein the surfactant comprises silicon.

18. The coated fiber of claim 11, wherein the surfactant is:

Si(CH$_3$)$_3$—O—[Si(CH$_3$)$_2$—O]$_x$—[SiR$^3$(CH$_3$)—O]$_y$—Si(CH$_3$)$_3$;

wherein R$^3$ is: —CH$_2$—CH$_2$—CH$_2$—(O—CH$_2$—CH$_2$)$_q$—(O—CH$_2$—CH$_2$—CH$_2$)$_r$—O—CO—CH$_3$ or —(O—CH$_2$—CH$_2$)$_q$—O—CO—CH$_3$;
wherein r, q, x, and y are average numbers of the respective repeat units.

19. The coated fiber of claim 11, wherein the organic fiber is linear polymeric fiber, carbon, poly(p-phenylene-2,6-benzobisoxazole), poly(p-phenylene terephthalamide), high molecular weight polyethylene, poly(4-oxybenzoate-co-2,6-oxynaphthoate), polyethylene terephthalate, or poly(pyridobisimidazole-2,6-diyl-(2,5-dihydroxy-p-phenylene)) fiber.

20. The coated fiber of claim 11, wherein the coating is the polymer or the thermoset.

21. A coated fiber comprising:
an organic fiber; and
a coating on the organic fiber comprising a siloxane-carborane polymer or a thermoset or ceramic made therefrom;
wherein the siloxane-carborane polymer or thermoset or ceramic made therefrom is made from a hydrosilation reaction of a siloxane-carborane compound containing at least two unsaturated carbon-carbon bonds and a silane compound;
wherein the organic fiber is linear polymeric fiber, poly(p-phenylene-2,6-benzobisoxazole), poly(p-phenylene terephthalamide), high molecular weight polyethylene, poly(4-oxybenzoate-co-2,6-oxynaphthoate), polyethylene terephthalate, or poly(pyridobisimidazole-2,6-diyl-(2,5-dihydroxy-p-phenylene)) fiber.

22. The coated fiber of claim 21:
wherein the siloxane-carborane compound has the formula:

U—(SiR$_2$—O)$_m$—SiR$_2$—CB$_{10}$H$_{10}$C—SiR$_2$—(O—SiR$_2$)$_m$-U; and wherein the silane compound has the formula:

H—SiR$_2$—(O—SiR$^1$R$^2$)$_n$—O—SiR$_2$—H;

wherein each R is an independently selected organic group;
wherein each R$^1$ is independently selected from H, R, methyl, phenyl, and —O—SiR$_2$—H;
wherein each R$^2$ is independently selected from H, R, methyl, and —O—SiR$_2$—H;
wherein each U is an independently selected group containing an unsaturated carbon-carbon bond; and
wherein each m and n is an independently selected positive integer.

23. The coated fiber of claim 22, wherein each R is methyl, each m is 1, and each U is vinyl or ethynyl.

24. The coated fiber of claim 22, wherein the silane compound is tetrakis(dimethylsiloxy)silane, methyltris(dimethylsiloxy)silane, phenyltris(dimethylsiloxy)silane, or 1,1,3,3,5,5-hexamethyltrisiloxane.

* * * * *